(12) United States Patent
Fraley et al.

(10) Patent No.: US 6,960,590 B2
(45) Date of Patent: Nov. 1, 2005

(54) ORALLY ACTIVE SALTS WITH TYROSINE KINASE ACTIVITY

(75) Inventors: Mark E. Fraley, North Wales, PA (US); Shyam B. Karki, Lansdale, PA (US); Yuntae Kim, Harleysville, PA (US)

(73) Assignee: Merck & Co. Inc., Rahway, NJ (US)

( * ) Notice: Subject to any disclaimer, the term of this patent is extended or adjusted under 35 U.S.C. 154(b) by 161 days.

(21) Appl. No.: 10/398,851

(22) PCT Filed: Oct. 17, 2001

(86) PCT No.: PCT/US01/32508

§ 371 (c)(1),
(2), (4) Date: Apr. 10, 2003

(87) PCT Pub. No.: WO02/32861

PCT Pub. Date: Apr. 25, 2002

(65) Prior Publication Data

US 2004/0002501 A1 Jan. 1, 2004

Related U.S. Application Data

(60) Provisional application No. 60/241,043, filed on Oct. 17, 2000.

(51) Int. Cl.[7] .............................................. A61K 31/496
(52) U.S. Cl. .................................. 514/253.07; 544/363
(58) Field of Search .................................... 514/253.07

(56) References Cited

U.S. PATENT DOCUMENTS 5,409,930 A 4/1995 Spada et al.
6,656,942 B2 * 12/2003 Fraley et al. .......... 514/253.07

FOREIGN PATENT DOCUMENTS

| WO | WO 92/20642 | 11/1992 |
|----|----|----|
| WO | WO 97/06144 | 2/1997 |
| WO | WO 97/19927 | 6/1997 |
| WO | WO 97/44037 | 11/1997 |
| WO | WO 98/23613 | 6/1998 |
| WO | WO 00/09495 | 2/2000 |
| WO | 01/29025 | * 4/2001 |

OTHER PUBLICATIONS

Greenberg, Drug News Perspect, vol. 11, pp. 265–270 (1998).*
Strawn et al. Exp. Opin. Invest. Drugs, vol. 7, pp. 553–573 (1998).*
Dredge et al. Expert Opin. Biol. Ther. vol. 2, pp. 953–966 (2002).*
Chinese Science Bulletin, vol. 36, No. 24, pp. 2056–2060 (1991), by J. Meng, et al.
Science in China, vol. 36, No. 5, pp. 540–549 (1993), by J. Meng, et al.
Oncogene, vol. 6, pp. 1677–1683 (1991), by B. Terman, et al.
J. Clin. Invest, vol. 104, No. 11, pp. 1613–1620 (1999), by N. van Bruggen, et al.
Drug News Perspect, vol. 11, No. 5, pp. 265–270 (1998), by D. Greenberg.
Nature, vol. 407, pp. 242–248 (2000), by G. Yancopoulos, et al.
Nature, vol. 407, pp. 249–257 (2000), by P. Carmeliet, et al.
J. Heterocyclic Chem., vol. 28, pp. 1481–1484 (1991), by J. Meng, et al.
Nature Biotech., vol. 17, pp. 963–968 (1999), by V. Brower.
Nature Medicine, vol. 5, No. 6, pp. 623–628 (1999), by H. Gerber, et al.
Molecular Cell, vol. 4, pp. 915–924 (1999), by B. Eliceirj, et al.
Stem Cells, vol. 12, pp. 1–6 (1994), by T. Burke, Jr.
Platelets, vol. 10, pp. 285–292 (1999), by A Amirkhosravi, et al.
FEBS Letters, vol. 473, pp. 161–164 (2000), by M. Nakagawa, et al.
Endocrinology, vol. 141, No. 5 pp. 1667–1674 (2000), by M. Deckers, et al.
Oncogene, vol. 5, pp. 519–524 (1990), by M. Shibuya, et al.
J. Med. Chem., vol. 37, pp. 2129–2137 (1994), by M. Maguire, et al.
J. Med. Chem., vol. 42, pp. 5369–5389 (1999), by L. Hennequin, et al.

* cited by examiner

*Primary Examiner*—Emily Bernhardt
(74) *Attorney, Agent, or Firm*—Sylvia A. Ayler; Valerie J. Camara

(57) ABSTRACT

The present invention relates to orally active salts of compounds which inhibit, regulate and/or modulate tyrosine kinase signal transduction, compositions which contain these compounds, and methods of using them to treat tyrosine kinase-dependent diseases and conditions, such as angio-genesis, cancer, tumor growth, atherosclerosis, age related macular degeneration, diabetic retinopathy, inflammatory diseases, and the like in mammals.

5 Claims, 3 Drawing Sheets

ORALLY ACTIVE SALTS WITH TYROSINE KINASE ACTIVITY

This application is a 371 of PCT/US01/32508, filed Oct. 17, 2001 which claims the benefit of U.S. Provisional Application No. 60/241,043, filed Oct. 17, 2000.

BACKGROUND OF THE INVENTION

The present invention relates to orally active salts of compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases play critical roles in signal transduction for a number of cell functions via substrate phosphorylation and have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endo-thelial cells, and the formation and sprouting of blood vessels, termed vasculogenesis and angiogenesis, respectively.

Angiogenesis is characterized by excessive activity of vascular endo-thelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Although quinolinyl-indole compounds have been previously reported to be useful as tyrosine kinase inhibitors (see WO 01/29025; published 26 Apr. 2001), a need still exists for forms of these compounds that can be readily administered to patients, especially orally active, soluble forms of these compounds. Accordingly, the identification of orally active salts of compounds which specifically inhibit, regulate and/or modulate the signal transduction of tyrosine kinases is desirable and is an object of this invention. The salts of the present invention have unexpectedly enhanced pharmokinetic properties as compared to compounds previously reported.

SUMMARY OF THE INVENTION

The present invention relates to salts of compounds that are capable of inhibiting, modulating and/or regulating signal transduction of both receptor-type and non-receptor type tyrosine kinases. The salts of the instant invention comprise salts of generic Formula I:

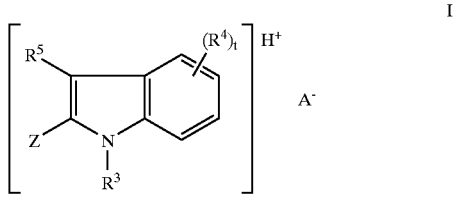

DETAILED DESCRIPTION OF THE INVENTION

Figure 1:
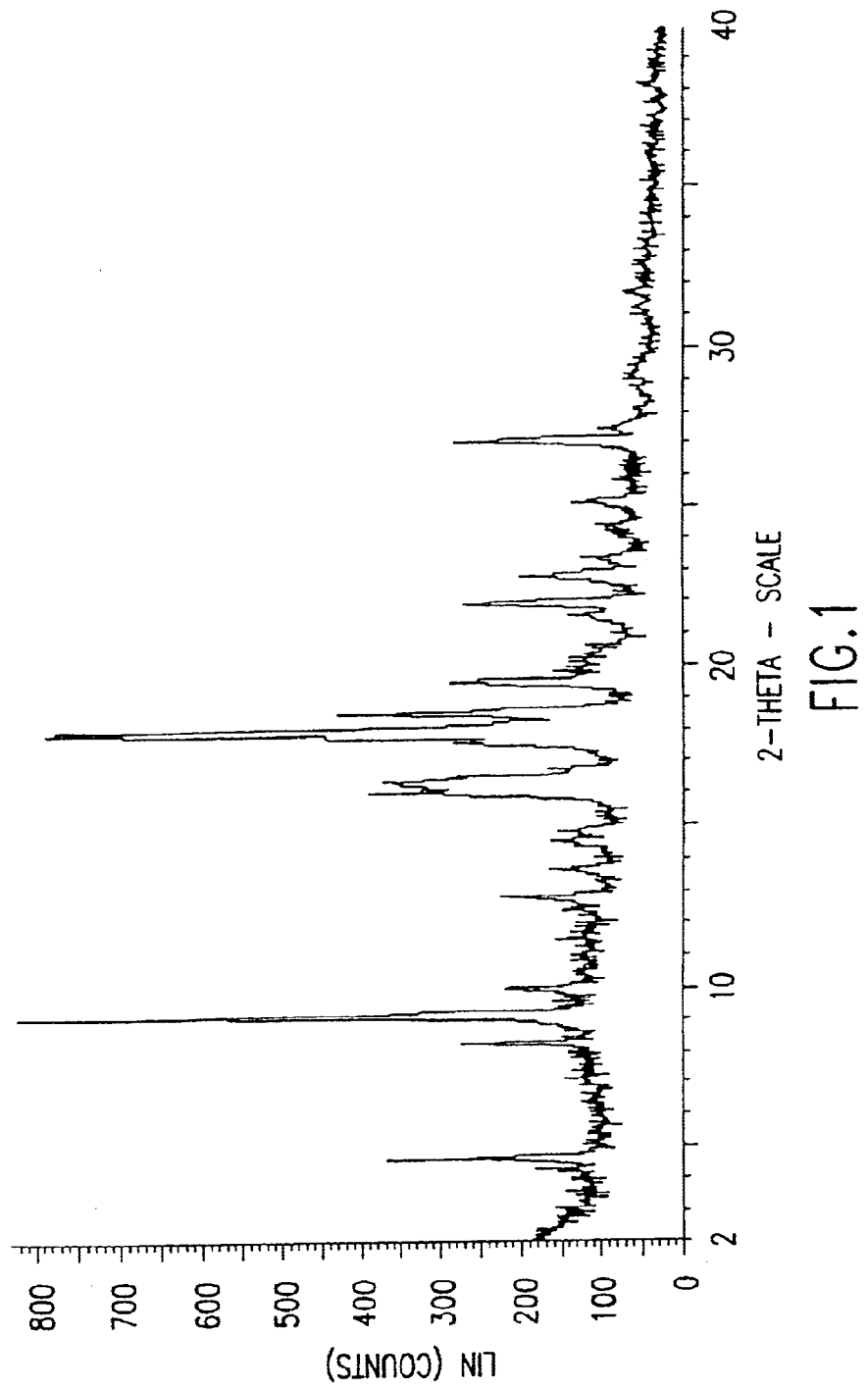
FIG. 1: X-ray powder diffraction pattern of the free base of 3-[5-(4-methanesulfonyl-piperazin-1-ylmethyl)-1H-indol-2-yl]-1H-quinolin-2-one (1-10).

An embodiment of the invention is illustrated by a mesylate salt 3-[5-(4-methanesulfonyl-piperazin-1-ylmethyl)-1H-indol-2-yl]-1H-quinolin-2-one.

Another embodiment is a chloride salt 3-[5-(4-methanesulfonyl-piperazin-1-ylmethyl)-1H-indol-2-yl]-1H-quinolin-2-one.

Also included in the scope of the invention is the mesylate salt of 3-[5-(4-methanesulfonyl-piperazin-1-ylmethyl)-1H-indol-2-yl]-1H-quinolin-2-one according to in crystalline form characterized by an X-ray powder diffraction pattern having diffraction angles of: 7.39, 8.20, 9.03, 9.90, 10.94, 15.45, 17.12, 17.84, 18.29, 18.64, 19.24, 19.77, 20.28, 21.73, 22.49, 23.27, 24.15, 24.73, 25.40, 26.79, and 27.50.

A further embodiment is the mesylate salt of 3-[5-(4-methanesulfonyl-piperazin-1-ylmethyl)-1H-indol-2-yl]-1H-quinolin-2-one in crystalline form characterized by an X-ray powder diffraction pattern having diffraction angles of: 6.94, 8.01, 9.74, 10.47, 10.77, 11.75, 12.61, 14.02, 15.28, 15.86, 16.93, 17.61, 18.69, 19.04, 19.47, 20.11, 21.56, 21.94, 22.53, 23.85, and 27.22.

Another embodiment is the chloride salt of 3-[5-(4-methanesulfonyl-piperazin-1-ylmethyl)-1H-indol-2-yl]-1H-quinolin-2-one in crystalline form characterized by an X-ray powder diffraction pattern having diffraction angles of: 7.08, 7.86, 8.99, 14.54, 15.40, 16.14, 16.81, 18.06, 19.91, 20.72, 22.72, 24.11, 26.09, 28.67, and 29.89.

And yet another embodiment is the chloride salt of 3-[5-(4-methanesulfonyl-piperazin-1-ylmethyl)-1H-indol-2-yl]-1H-quinolin-2-one in crystalline form characterized by an X-ray powder diffraction pattern having multiple diffraction peaks between 5° and 30° 2-theta and a melting endotherm of 284.08° C. at a rate of 10° C. per minute.

Also included in the scope of the invention is a mesylate salt of 3-[5-(4-methyl-5-oxo-[1,4]diazepan-1-ylmethyl)-1H-indol-2-yl]-1H-quinolin-2-one.

And yet another embodiment is a chloride salt of 3-[5-(4-methyl-5-oxo-[1,4]diazepan-1-ylmethyl)-1H-indol-2-yl]-1H-quinolin-2-one.

And still another embodiment is a mesylate salt of 3-{5-[4-(2-hydroxy-ethanoyl)-piperazin-1-ylmethyl]-1H-indol-2-yl}-1H-quinolin-2-one.

A further embodiment is a chloride salt of 3-{5-[4-(2-hydroxy-ethanoyl)-piperazin-1-ylmethyl]-1H-indol-2-yl}-1H-quinolin-2-one.

Another embodiment is the chloride salt 3-{5-[4-(2-hydroxy-ethanoyl)-piperazin-1-ylmethyl]-1H-indol-2-yl}-1H-quinolin-2-one in crystalline characterized by a reversible endotherm at 235° C. at a scan rate of 10° C. per minute.

And a still another embodiment is a mesylate salt of 3-(5-{2-[(2-methoxyethyl)(methyl)amino]ethoxy}-1H-indol-2-yl)quinolin-2(1H)-one.

A further embodiment is the mesylate salt of 3-(5-{2-[(2-methoxyethyl)(methyl)amino]ethoxy}-1H-indol-2-yl)quinolin-2(1H)-one in crystalline form characterized by multiple reversible endotherms at 82° C., 151.4° C., and 229° C. at a scan rate of 10° C. per minute.

And another embodiment is a mesylate or chloride salt of 3-[5-(4-methanesulfonyl-piperazin-1-ylmethyl)-1H-indol-2-yl]-1H-quinolin-2-one; 3-[5-(4-methyl-5-oxo-[1,4]diazepan-1-ylmethyl)-1H-indol-2-yl]-1H-quinolin-2-one; 3-{5-[4-(2-hydroxy-ethanoyl)-piperazin-1-ylmethyl]-1H-indol-2-yl}-1H-quinolin-2-one; or 3-(5-{2-[(2-methoxyethyl)(methyl)amino]ethoxy}-1H-indol-2-yl)quinolin-2(1H)-one.

Also included within the scope of the claims is a pharmaceutical composition which is comprised of a salt of the present invention and a pharmaceutically acceptable carrier. The present invention also encompasses a method of treating or preventing cancer in a mammal in need of such treatment which is comprised of administering to said mammal a therapeutically effective amount of a presently disclosed salt. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a salt of Formula I. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a salt of Formula I. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a salt of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of a salt of Formula I is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed salts in combination with a second compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combreta-statin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a salt of Formula I in combination with radiation therapy and/or in combination with a compound selected from:

1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a salt of Formula I in combination with paclitaxel or trastuzumab.

Also within the scope of the invention is a method of reducing or preventing tissue damage following a cerebral ischemic event which comprises administering a therapeutically effective amount of a salt of Formula I.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The salts of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the salts disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

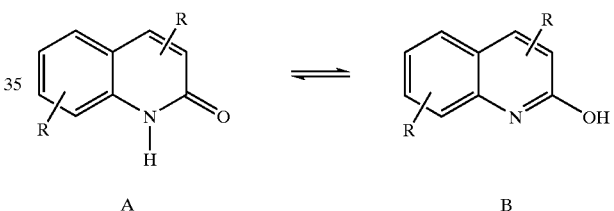

Utility

The instant salts are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like). Based on pharmacokinetic studies in animals, the prsently claimed salts have an unexpectedly superior oral activity profile compared to the corresponding free base and are therefore particularly suited for oral administration. They may, however, be adminsitered via other routes as described herein.

The salts of the instant invention may be administered to patients for use in the treatment of cancer. The instant salts inhibit tumor angiogenesis, thereby affecting the growth of tumors (J. Rak et al. *Cancer Research,* 55:4575–4580, 1995). The anti-angiogenesis properties of the instant salts are also useful in the treatment of certain forms of blindness related to retinal vascularization.

The disclosed salts are also useful in the treatment of certain bone-related pathologies, such as osteosarcoma, osteoarthritis, and rickets, also known as oncogenic osteomalacia. (Hasegawa et al., Skeletal Radiol., 28, pp. 41–45, 1999; Gerber et al., Nature Medicine, Vol. 5, No. 6, pp. 623–628, June 1999). And since VEGF directly promotes osteoclastic bone resorption through KDR/Flk-1 expressed in mature osteoclasts (FEBS Let. 473:161–164 (2000); Endocrinology, 141:1667 (2000)), the instant salts are also useful to treat and prevent conditions related to bone resorption, such as osteoporosis and Paget's disease.

The claimed salts can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999).)

The salts of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice.

For oral use of a chemotherapeutic compound according to this invention, the compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

The salts of the instant invention may also be co-administered with other well known therapeutic agents that are selected for their particular usefulness against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336,156 (Pfizer) and lasofoxifene; cathespin K inhibitors; and ATP proton pump inhibitors.

The instant salts are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-yridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)enzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl] acridine-2-(6H)propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)dione, lurtotecan, 7-[2-(N-isopropylamino)ethyl]-(20S) camptothecin, BNP 1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido [4,3-b]carbazole-1-carboxamide, asulacrine, (5a,5aB,8aa, 9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin- 6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820, 850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342, 952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

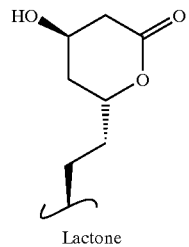

Lactone

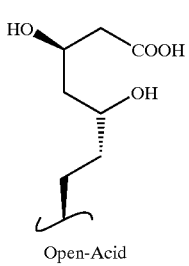

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesylprotein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-Hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-Oxo-2H-[1,2']bipyridin-5'-ylmethyl]-3H-imidazol-4-ylmethyl}benzonitrile, 4-[3-(2-Oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-Dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclo-oxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin. Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp. 963–968 (October 1999); Kim et al., Nature, 362, 841–844 (1993)).

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\alpha_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10, 11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4'-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instantly claimed salts are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, Platelets 10, 285–292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the salts of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the salts of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

Assays

The compounds of the instant invention described in the Examples were tested by the assays described below and were found to have kinase inhibitory activity. Other assays are known in the literature and could be readily performed by those of skill in the art (see, for example, Dhanabal et al., Cancer Res. 59:189–197; Xin et al., J. Biol. Chem. 274:9116–9121; Sheu et al., Anticancer Res. 18:4435–4441; Ausprunk et al., Dev. Biol. 38:237–248; Gimbrone et al., J. Natl. Cancer Inst. 52:413–427; Nicosia et al., In Vitro 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 µg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 µl of inhibitor or control to the assay in 50% DMSO.

2. Add 35 µl of reaction mix containing 5 µl of 10× reaction buffer, 5 µl 25 mM ATP/10 µCi [$^{33}$P]ATP (Amersham), and 5 µl 10× substrate.

3. Start the reaction by the addition of 10 µl of KDR (25 nM) in enzyme dilution buffer.

4. Mix and incubate at room temperature for 15 minutes.

5. Stop by the addition of 50 µl stop solution.

6. Incubate for 15 minutes at 4° C.

7. Transfer a 90 µl aliquot to filter plate.

8. Aspirate and wash 3 times with wash solution.

9. Add 30 µl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 1–5 below.

Culture Plates: NUNCLON 96-well polystyrene tissue culture plates (NUNC #167008).

Assay Medium: Dulbecco's modification of Eagle's medium containing 1 mg/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human VEGF$_{165}$ (500 ng/mL; R&D Systems) and bFGF (10 ng/mL; R&D Systems) are prepared in Assay Medium.

10× [$^3$H]Thymidine: [Methyl-$^3$H]thymidine (20 Ci/mmol; Dupont-NEN) is diluted to 80 µCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) Na$_2$CO$_3$.

Method

1. HUVEC monolayers maintained in EGM are harvested by trypsinization and plated at a density of 4000 cells per 100 µL Assay Medium per well in 96-well plates. Cells are growth-arrested for 24 hours at 37° C. in a humidified atmosphere containing 5% CO$_2$.

2. Growth-arrest medium is replaced by 100 µL Assay Medium containing either vehicle (0.25% [v/v] DMSO) or the desired final concentration of test compound. All determinations are performed in triplicate. Cells are then incubated at 37° C. with 5% CO$_2$ for 2 hours to allow test compounds to enter cells.

3. After the 2-hour pretreatment period, cells are stimulated by addition of 10 µL/well of either Assay Medium, 10×VEGF solution or 10×bFGF solution. Cells are then incubated at 37° C. and 5% CO$_2$.

4. After 24 hours in the presence of growth factors, 10× [$^3$H]thymidine (10 µL/well) is added.

5. Three days after addition of [$^3$H]thymidine, medium is removed by aspiration, and cells are washed twice with Cell Wash Medium (400 µL/well followed by 200 µL/well). The washed, adherent cells are then solubilized by addition of Cell Lysis Solution (100 µL/well) and warming to 37° C. for 30 minutes. Cell lysates are transferred to 7-mL glass scintillation vials containing 150 µL of water. Scintillation cocktail (5 mL/vial) is added, and cell-associated radioactivity is determined by liquid scintillation spectroscopy.

Based upon the foregoing assays the compounds of the present invention are inhibitors of VEGF and thus are useful for the inhibition of angio-genesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.01–5.0 µM. These compounds may also show selectivity over related tyrosine kinases (e.g., FGFR1 and the Src family; for relationship between Src kinases and VEGFR kinases, see Eliceiri et al., Molecular Cell, Vol. 4, pp. 915–924, December 1999).

III. Flt-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.

2. The appropriate amount of reaction mix was prepared at room temperature:
   10× Buffer (20 mM Tris pH 7.4/0.1 M NaCl/1 mM DTT final)
   0.1M MnCl$_2$ (5 mM final)
   pEY substrate (75 µg/mL)
   ATP/[$^{33}$P]ATP (2.5 µM/1 µCi final)
   BSA (500 µg/mL final).

3. 5 µL of the diluted inhibitor was added to the reaction mix. (Final volume of 5 µL in 50% DMSO). To the positive control wells, blank DMSO (50%) was added.

4. 35 µL of the reaction mix was added to each well of a 96 well plate.

5. Enzyme was diluted into enzyme dilution buffer (kept at 4° C.).

6. 10 μL of the diluted enzyme was added to each well and mix (5 nM final). To the negative control wells, 10 μL 0.5 M EDTA was added per well instead (final 100 mM).
7. Incubation was then carried out at room temperature for 30 minutes.
8. Stopped by the addition of an equal volume (50 μL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 μL per wash).
12. Allowed to dry under vacuum for 2–3 minutes.
13. Dryed in hood for ~20 minutes.
14. Assembled Wallac Millipore adapter and added 50 μL of scintillant to each well and counted.

IV. Flt-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:
1. Dilute inhibitors (account for the final dilution into the assay, 1:20)
2. Prepare the appropriate amount of reaction mix at room temperature.
   10X Buffer (20 mM Tris pH 7.4/0.1 M NaCl/1 mM DTT final)
   0.1M $MnCl_2$ (5 mM final)
   pEY substrate (75 μg/mL)
   ATP/[$^{33}$P]ATP (0.5 μM/L μCi final)
   BSA (500 μg/mL final)
3. Add 5 μL of the diluted inhibitor to the reaction mix. (Final volume of 5 μL in 50% DMSO). Positive control wells—add blank DMSO (50%).
4. Add 35 μL of the reaction mix to each well of a 96 well plate.
5. Dilute enzyme into enzyme dilution buffer (keep at 4° C.).
6. Add 10 μL of the diluted enzyme to each well and mix (5–10 nM final). Negative control wells—add 10 μL 0.5 M EDTA per well instead (final 100 mM)
7. Incubate at room temperature for 60 minutes.
8. Stop by the addition of an equal volume (50 μL) of 30% TCA/0.1M Na pyrophosphate.
9. Incubate for 15 minutes to allow precipitation.
10. Transfer to Millipore filter plate.
11. Wash 3× with 15% TCA/0.1M Na pyrophosphate (125 μL per wash).
12. Allow to dry under vacuum for 2–3 minutes.
13. Dry in hood for ~20 minutes.
14. Assemble Wallac Millipore adapter and add 50 μL of scintillant to each well and count.

EXAMPLES

Examples provided are intended to assist in a further understanding of the invention. Particular materials employed, species and conditions are intended to be illustrative of the invention and not limiting of the reasonable scope thereof.

The free bases used to prepare the salts of this invention may be obtained by employing the procdures described below as well as those disclosed in WO 01/29025, published 26 Apr. 2001, hereby incorporated by reference. In addition, other procedures may be used by standard manipulations of reactions that are known in the literature.

HPLC Methods Used:

| Isocratic method (for solubility studies) | |
| --- | --- |
| Column: | BDS HYPESIL, C18 (250 mm × 46 mm), 5 μm particle size |
| Column Temperature: | ambient |
| Detector: | 230 nm (UV wavelength) |
| Column Temp. | ambient |
| Flow Rate: | 1.0 mL/min |
| Injection Volume: | 20 μL |
| Mobile Phase: | A) 0.1% Phosphoric Acid B) 100% Acetonitrile |
| Diluent: | 50% Acetonitrile-DI water |
| Gradient Profile: | (A/B) starts from (60/40) and stays at (60/40) for 20 minutes. |
| Run Time: | 20 minutes |

Example 1

Salts of 3-[5-(4-Methanesulfonyl-piperazin-1-ylmethyl)-1H-indol-2-yl]-1H-quinolin-2-one (1-11)

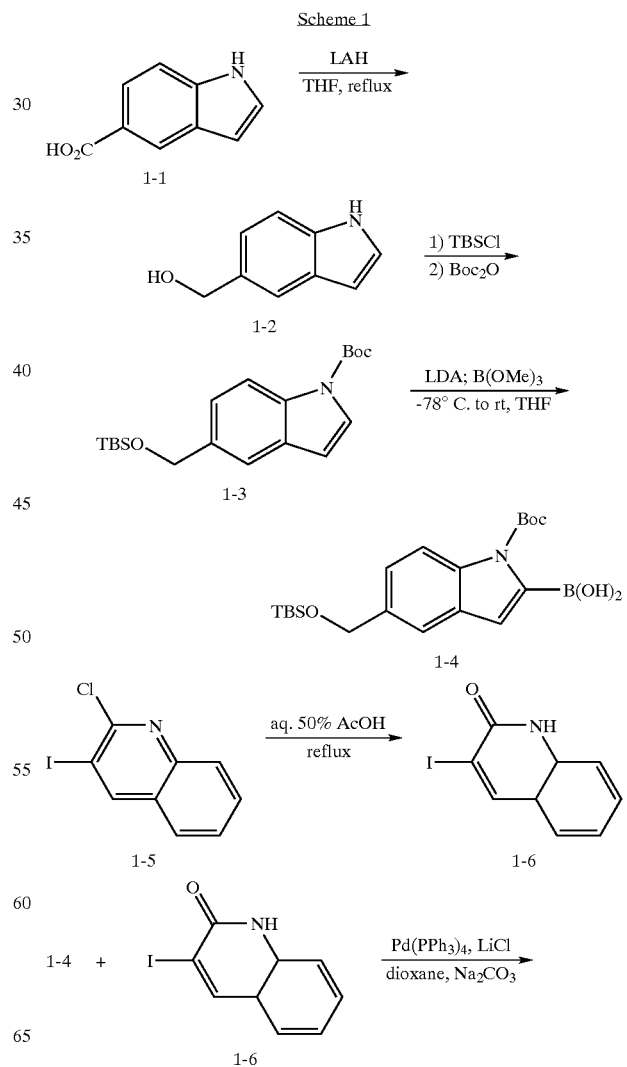

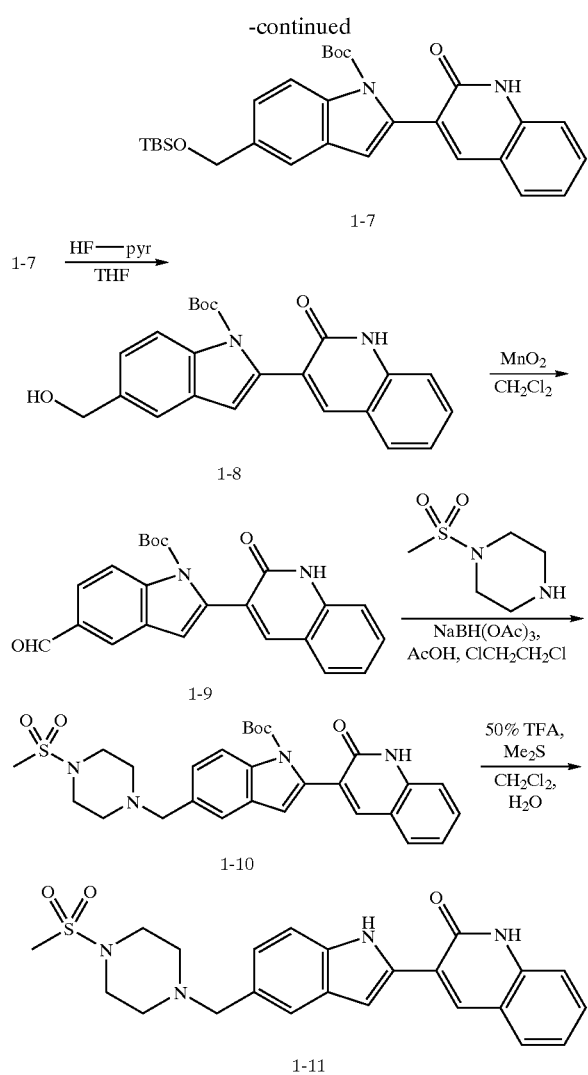

(1H-Indol-5-yl)-methanol (1-2)

To a mechanically stirred solution of 1H-Indole-5-carboxylic acid (1-1, 20.01 g, 124 mmol) in THF (500 mL) was added at ambient temperature slowly a solution of 1M-LAH in toluene (186 mL, 186 mmol, 1.5 equiv). The reaction mixture was heated at reflux for 1 hour, quenched with ice, partitioned between ethylacetate and saturated aqueous $NaHCO_3$. The organic layer was washed with brine, separated, dried ($MgSO_4$) and concentrated in vacuo. The crude product solidified upon standing under the reduced pressure. The crude solid was suspended in hexanes (200 mL) and ethyl acetate (10 mL), stirred overnight, collected by filtration and air-dried to afford the desired product as a light brown solid. $^1$H NMR (400 MHz, $CDCl_3$) δ 8.24 (br s, 1H), 7.62 (s, 1H), 7.36 (d, 1H, J=8.4 Hz), 7.23 (d, 1H, J=8.4 Hz), 7.20 (s, 1H), 6.54 (s, 1H), 4.75 (s, 2H), 1.68 (s, 1H).

5-(tert-Butyl-dimethyl-silanyloxymethyl)-indole-1-carboxylic acid tert-butyl ester (1-3)

A stirred solution of (1H-Indol-5-yl)-methanol (1-2, 16.5 g, 112.1 mmol) in dichloromethane (300 mL) was subsequently treated at ambient temperature with diisopropylethylamine (39 mL, 224.2 mmol, 2 equiv), tert-butyldimethylsilyl chloride (18.6 g, 123.3 mmol, 1.1 equiv), and 4-(N,N-dimethylamino)pyridine (1.37 g, 11.2 mmol, 0.1 equiv). The reaction mixture was stirred at room temperature for 30 minutes, concentrated in vacuo, partitioned between ethyl acetate and 0.5N-HCl. The organic layer was washed with brine, separated, dried ($MgSO_4$), concentrated in vacuo to give the crude silylether as a light brown solid. The crude product and di-tert-butyl dicarbonate (26.9, 123.3 mmol) were dissolved in dichrolomethane (300 mL) and stirred at ambient temperature in the presence of 4-(N,N-dimethylamino) pyridine (1.37 g, 11.2 mmol) for 2 hours. The reaction mixture was concentrated in vacuo, partitioned between ethyl acetate and 0.5N-HCl. The organic layer was washed with brine, separated, dried ($MgSO_4$) and concentrated in vacuo to give the crude oil. Chromatography ($SiO_2$, 10% ethyl acetate in hexanes) afforded 5-(tert-Butyl-dimethyl-silanyloxymethyl)-indole-1-carboxylic acid tert-butyl ester (1-3) as a white solid; $^1$H NMR (400 MHz, $CDCl_3$) δ 7.97 (d, 1H, J=8.0 Hz), 7.47 (d, 1H, J=3.2 Hz), 7.41 (s, 1H), 7.15 (d, 1H, J=7.7 Hz), 6.44 (d, 1H, J=3.6 Hz), 4.72 (s, 2H), 1.56 (s, 9H), 0.84 (s, 9H), 0.00 (s, 6H).

5-(tert-Butyl-dimethyl-silanyloxymethyl)-indole-1-tert-butyloxycarbonylindole-2-boronic acid (1-4)

To a stirred solution of 5-(tert-Butyl-dimethyl-silanyloxymethyl)-indole-1-carboxylic acid tert-butyl ester (1-3, 38.6 g, 106.7 mmol) in tetrahydrofuran (400 mL) was slowly added at −78° C. a solution of lithiun diisopropylamide in tetrahydrofuran (2M, 80.1 mL, 160.1 mmol, 1.5 equiv). The reaction mixture was stirred at the same temperature for 1 hour, treated with trimethylborate, warmed up to ambient temperature, and partitioned between ethyl acetate and 0.5N-HCl. The organic layer was washed with brine, separated, dried ($MgSO_4$) and concentrated in vacuo to give the crude solid. Trituation of the crude product with hexanes followed by filtration and air-drying afforded the desired boronic acid (1-4) as a white powder. $^1$H NMR (400 MHz, $CDCl_3$) δ 7.96 (d, 1H, J=6.8 Hz), 7.54 (s, 1H), 7.47 (s, 1H), 7.32 (d, 1H, J=6.8 Hz), 7.10 (s, 1H), 4.82 (s, 2H), 1.74 (s, 9H), 0.95 (s, 9H), 0.11 (s, 6H).

3-Iodo-1H-quinolin-2-one (1-6)

The 2-chloro-3-iodoquinoline (1-5, 30.0 g) was weighed into a 250 mL flask and suspended in of 50% aqueous acetic acid (125 mL). The mixture was heated to 100° C. and allowed to reflux for 16 hours to completion by TLC analysis of the crude reaction mixture. The mixture was allowed to cool to ambient temperature followed by dilution with 200 mL of water. The resulting suspension of the desired product was isolated by vacuum filtration follows by washing with water (50 mL). The water and traces of acetic acid were removed under vacuum for 5 hours to afford the desired quinolinone as a tan powder (1-6). $^1$H NMR (500 MHz, $CDCl_3$) δ 12.13 (br s, 1H), 8.71 (s, 1H), 7.65 (d, 1H, J=7.5 Hz), 7.54 (m, 1H), 7.31 (d, 1H, J=8.0 Hz), 7.20 (m, 1H).

5-Hydroxymethyl-2-(2-oxo-1,2-dihydro-quinolin-3-yl)-indole-1-carboxylic acid tert-butyl ester (1-8)

A stirred mixture of the iodoquinolinone (1-6, 10 g, 36.9 mmol, 1 equiv), the boronic acid (1-4, 7.5 g, 18.45 mmol, 0.5 equiv), tetrakis (triphenyl-phosphine) palladium (1.71 g, 1.48 mmol, 0.04 equiv), and lithium chloride (4.69 g, 110.7 mmol, 3 equiv) in dioxane/2M-aqueous $Na_2CO_3$ was degassed and heated at 80° C. until the boronic acid is not detected by thin layer chromatography. Additional boronic acid (0.2 equiv at a time) was added to the reaction mixture until all the iodoquinolinone (1-6) was consumed completely (1.5 equivalent of the boronic acid, 1-4, in total, was required). The reaction mixture was partitioned between ethyl acetate and saturated aqueous $NaHCO_3$. The organic layer was washed with brine, separated, dried ($MgSO_4$) and concentrated in vacuo. The crude oil (1-7) was dissolved in tetrahydrofuran (100 mL), transferred to the PEG bottle, treated at 0° C. with HF-pyridine (15 mL) and stirred for 1 hour at ambient temperature. The reaction mixture was partitioned between ethyl acetate and saturated aqueous $NaHCO_3$. The organic layer was washed with brine, separated, dried ($MgSO_4$) and concentrated in vacuo. The crude solid was triturated with ethyl acetate and hexanes, collected by filtration and air-dried to afford the desired product (1-8) as a light yellow solid; $^1H$ NMR (500 MHz, DMSO-$d_6$) δ 12.1 (s, 1H), 8.07 (s, 1H), 8.03 (d, 1H, J=8.5 Hz), 7.74 (d, 1H, J=7.5 Hz), 7.55 (s, 1H), 7.52 (t, 1H, J=7.5 Hz), 7.35 (d, 1H, J=8.5 Hz), 7.30 (d, 1H, J=7.5 Hz), 7.22 (t, 1H, J=7.5 Hz), 6.77 (s, 1H), 5.21 (t, 1H, J=5.5 Hz), 4.60 (d, 2H, J=5.5 Hz), 1.35 (s, 9H).

5-Formyl-2-(2-oxo-1,2-dihydro-quinolin-3-yl)-indole-1-carboxylic acid tert-butyl ester (1-9)

The pre-activated $MnO_2$ (34.5 g, 15 equiv) and the alcohol (1-8, 10.32 g, 1.0 equiv) were weighed into a 1-liter flask and suspended in dry dichloromethane (500 mL). The reaction mixture was heated to 45° C. and was complete by thin layer chromatography after 1 hour. The mixture was allowed to cool to ambient temperature and the manganese oxide(s) were removed by vacuum filtration. The resulting pad of oxides on the filter were triturated with hot THF and the solvent filtered through under vacuum to remove any product from the oxides. The resulting filtrate was concentrated in vacuo to afford the crude aldehyde as a yellow solid. The solid was triturated with methanol (10 mL) and ethyl acetate (15 mL) followed by vacuum filtration to isolate the pure product. The light-yellow aldehyde was dried under vacuum (1-9). $^1H$ NMR (500 MHz, DMSO-$d_6$) δ 12.15 (s, 1H), 10.08 (s, 1H), 8.26 (d, 1H, J=1.5 Hz), 8.24 (d, 1H, J=8.5 Hz), 8.15 (s, 1H), 7.90 (dd, 1H, J=8.5, 1.5 Hz), 7.77 (d, 1H, J=7.5 Hz), 7.55 (m, 1H), 7.37 (d, 1H, J=8.5 Hz), 7.24 (m, 1H), 7.01 (s, 1H).

5-(4-Methanesulfonyl-piperazin-1-ylmethyl)-2-(2-oxo-1,2-dihydro-quinolin-3-yl)-indole-1-carboxylic acid tert-butyl ester (1-10)

To a stirred solution of the aldehyde (1-9, 2.01 g, 5.15 mmol, 1 equiv) and N-methanesulfonylpiperazine acetic acid salt (4.62 g, 20.60 mmol, 4 equiv) in dichloroethane (400 mL) was added at ambient temperature acetic acid (1.2 mL). The reaction mixture was treated with sodium triacetoxyborohydride and stirred for 3 hours. The reaction stopped at 76% of conversion and treated with $MgSO_4$ and additional 1 g of the hydride. After further stirring for 1 hour the reaction was complete. The reaction mixture was partitioned between ethyl acetate and saturated aqueous $NaHCO_3$. The organic layer was once again washed with saturated aqueous $NaHCO_3$, and then with brine, separated, dried with ($Na_2SO_4$) and concentrated in vacuo. The crude solid was dissolved in dimethylformamide and treated with the activated carbon. The filtrate solution (celite) was concentrated to syrup which was quickly triturated with methanol (100 mL). The resulting solid was collected by filtration, redissolved in dimethylformamide, concentrated to syrup, triturated with methanol (100 mL), collected by filtration and vacuum-dried to give 5-(4-Methanesulfonyl-piperazin-1-ylmethyl)-2-(2-oxo-1,2-dihydro-quinolin-3-yl)-indole-1-carboxylic acid tert-butyl ester (1-10) as a white powder; $^1H$ NMR (500 MHz, DMSO-$d_6$) δ 12.06 (s, 1H), 8.06 (s, 1H), 8.04 (d, 1H, J=8.5 Hz), 7.74 (d, 1H, J=8.0 Hz), 7.55 (s, 1H), 7.53 (dt, 1H, J=8.0, 1.5 Hz), 7.35 (d, 1H, J=8.5 Hz), 7.30 (dd, 1H, J=8.5, 1.5 Hz), 7.22 (t, 1H, J=7.5 Hz), 6.76 (s, 1H), 3.62 (s, 2H), 3.16 (m, 4H), 2.87 (s, 3H), 2.48 (m, 4H), 1.35 (s, 9H).

3-[5-(4-Methanesulfonyl-piperazin-1-ylmethyl)-1H-indol-2-yl]-1H-quinolin-2-one (1-11)

A mixture of 5-(4-Methanesulfonyl-piperazin-1-ylmethyl)-2-(2-oxo-1,2-dihydro-quinolin-3-yl)-indole-1-carboxylic acid tert-butyl ester (1-10, 1.02 g, 1.863 mmol), dimethylsulfide (1.2 mL), water (0.6 mL) and TFA (40 mL) in dichloromethane (40 mL) was stirred for 1.5 hours. The reaction mixture was concentrated in vacuo, partitioned between ethyl acetate and saturated aqueous $NaHCO_3$. The organic layer was washed with brine, separated, dried ($Na_2SO_4$), and concentrated in vacuo. The resulting crude solid was purified by reverse-phase liquid chromatography ($H_2O/CH_3CN$ gradient with 0.1% TFA present) to give trifluoroacetic acid salt of 1-11. All the fractions containing the desired product was partitioned between ethyl acetate and saturated aqueous $NaHCO_3$. The organic layer was washed with brine, separated, dried ($Na_2SO_4$), and concentrated in vacuo to give 3-[5-(4-Methanesulfonyl-piperazin-1-ylmethyl)-1H-indol-2-yl]-1H-quinolin-2-one (1-11) as a bright yellow solid; $^1H$ NMR (500 MHz, DMSO-$d_6$) δ 12.07 (s, 1H), 11.54 (s, 1H), 8.53 (s, 1H), 7.73 (d, 1H, J=7.5 Hz), 7.52 (t, 1H, J=7.5 Hz), 7.47–7.46 (m, 2H), 7.38 (d, 1H, J=8.5 Hz), 7.29 (br s, 1H), 7.25 (t, 1H, J=7.5 Hz), 7.08 (d, 1H, J=9.0 Hz), 3.57 (s, 2H), 3.11 (m, 4H), 2.87 (s, 3H), 2.48 (m, 4H).

Solubility of Free Bases:

The solubility of 1-11 at room temperature was determined in 0.05M aqueous buffers, water and several organic solvents. The results are tabulated in Tables I and II.

TABLE I pH Solubility Profile of 1-11

| Buffer | pH $_{final}$ | Solubility (mg/mL) |
|---|---|---|
| 0.05M Carbonate | 11.15 | 0.077 |
| 0.05M Carbonate | 10.09 | 0.079 |
| 0.05M Phosphate | 8.86 | 0.073 |
| 0.05M Phosphate | 7.93 | 0.074 |
| 0.05M Phosphate | 6.96 | 0.071 |
| 0.05M Citrate | 6.01 | 0.071 |
| 0.05M Citrate | 5.07 | 0.070 |
| 0.05M Citrate | 4.15 | 0.073 |
| 0.05M Citrate | 3.23 | 0.092 |
| 0.01 N HCl | 2.45 | 0.40 |

TABLE II

Solubility of 1-11 in several solvent systems and HPβCD.

| Solvent | Solubility (mg/mL) |
|---|---|
| Water | 0.00003 |
| Ethanol | 0.019 |
| Isopropanol | 0.0065 |
| Acetonitrile | 0.084 |
| 50% Aqueous Can | 0.060 |
| 25% HPβCD[1] | 0.168 |
| 25% HPβCD[2] | 4.56 |

TABLE II-continued

Solubility of 1-11 in several solvent systems and HPβCD.

| Solvent | Solubility (mg/mL) |
|---|---|
| 20% HPβCD[2] | 3.57 |
| 15% HPβCD[2] | 2.35 |
| 10% HPβCD[2] | 1.74 |

[1]Native pH in water (pH = 7.5)
[2]pH adjusted to ca. 3.0 with HCl.

As can be discerned from these tables, the free base has a very low solubility in water.

Measurement of Salt Solubility:

The solid free base was treated with a concentrated solution of the appropriate acid (1.05–1.1 molar equivalence) and suspended in water for several days. The pH and concentration of the compound in equilibrium with the solid phase was measured by HPLC (UV-Vis detection). This method overestimates the solubility of the salt due to the 5–10% excess of the acid that is added in the preparation of the salts. For the same reason, the pH's that are obtained are most likely lower than the pH of the salt in water. The results are shown below in Table III.

TABLE III

Salt Solubility

| Salt of 1-11 | Solubility (mg/mL) | pH |
|---|---|---|
| Mesylate | 0.58 | 2.3 |
| Tartrate | 0.90 | 2.4 |
| HCl | 0.43 | 2.3 |
| Citrate | 0.11 | 2.5 |
| Acetate | 0.091 | 3.3 |
| HBr | 0.20 | 2.9 |
| Maleate | 0.16 | 2.5 |
| Sulfate | 0.13 | 1.5 |
| Besylate | 0.0038 | 2.4 |

Physical Properties of the Mesylate Salt of 1-11:

The mesylate salt of 1-11 has molecular formula $C_{24}H_{28}N_4O_6S_2$ and a molecular weight of 532.642. Three forms of the mesylate salt of 1-11 have been observed: one amorphous salt and two crystalline salts. Initially an amorphous solid was obtained as determined by optical microscopy under plane polarized light.

The amorphous mesylate salt was recrystallized from 50:50 Ethanol:THF to give a crystalline powder (Salt 1-11A). The X-ray powder diffraction pattern (XRPD) of the recrystallized mesylate salt 1-11A (FIG. 2) is indicative of crystalline material with multiple diffraction peaks between 5° and 30° 2-theta. DSC of this material from 20° C. to 350° C. at a heating rate of 10° C./minute shows a sharp endotherm at 266° C. which is attributed to melting. TGA of this material from 20° C. to 350° C. at a heating rate of 10° C./minute showed a weight loss of 1.25% between 20° C. and 125° C., attributable to residual solvent. This mesylate salt has a solubility in water of 0.173 mg/mL.

TABLE IV

Solubility of Salt 1-11A

| Solvent | Solubility (mg/mL) |
|---|---|
| Water | 0.173 |
| Isopropanol | 0.02 |
| Acetonitrile | 0.063 |

Figure 2:
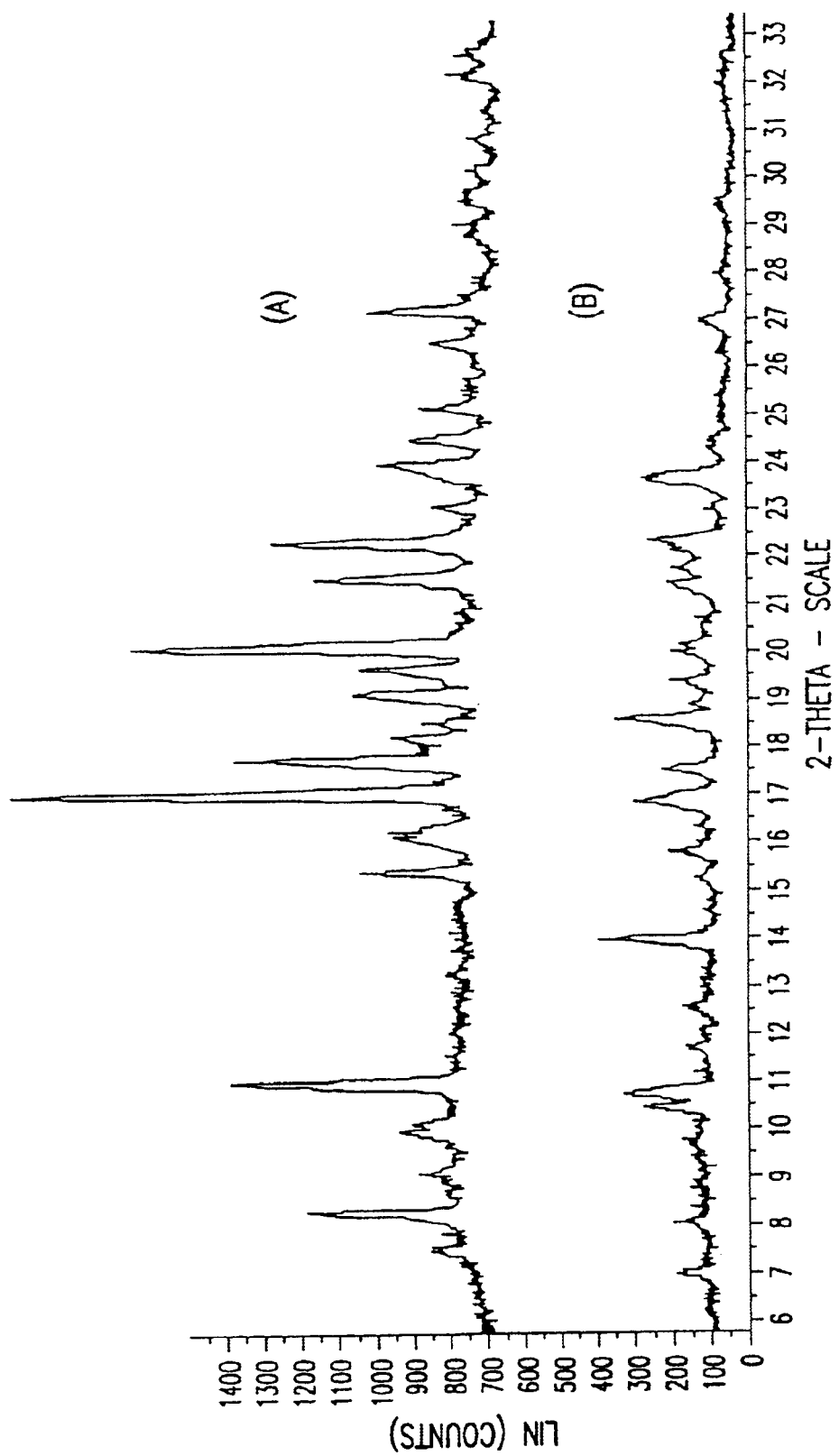
FIG. 2: X-ray powder diffraction pattern of crystalline forms of the mesylate salt of 3-[5-(4-methanesulfonyl-piperazin-1-ylmethyl)-1H-indol-2-yl]-1H-quinolin-2-one (A) Salt 1-10A (B) Salt 1-10B.

A second batch of crystalline mesylate salt (Salt 1-11B) was obtained by the following procdeure. To a stirred suspension of 1-11 (4.026 g, 9.22 mmol) in MeOH was slowly added at room temperature (RT) one equivalent of a 0.3M solution of methanesulfonic acid (30.73 mL). After all the solid had dissolved, the mixture was filtered into a flask and concentrated under reduced pressure while cooled to about 10° C. The resulting solid was suspended with 200 mL of ethylacetate, filtered, and dried to afford the mesylate salt. This salt was found to be crystalline by XRPD (FIG. 2). This crystalline form is different by XRPD than the one recrystallized from the amorphous salt in EtOH/THF (Salt 1-11A). This form has a lower solubility in water 0.09 mg/mL than Salt 1-11A suggesting it is a more stable form of the mesylate salt. The solubilities of Salt 1-11B are summarized in Table V below:

TABLE V

Solubility of Salt 1-11B

| Solvent | Solubility (mg/mL) |
|---|---|
| Water | 0.09 |
| Isopropanol | 0.003 |
| Acetonitrile | 0.03 |

Figure 3:
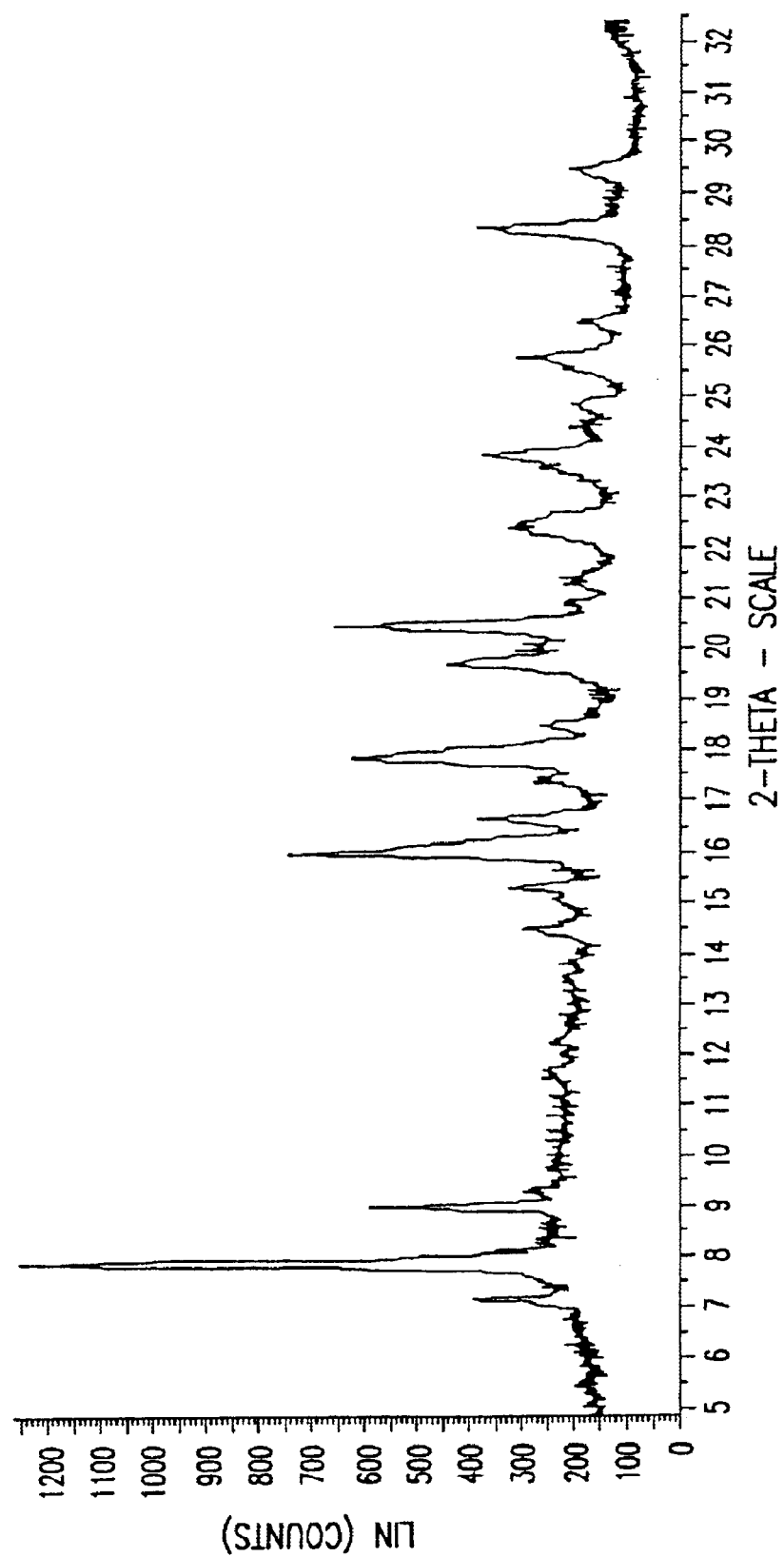
FIG. 3: X-ray powder diffraction pattern of crystalline HCl salt of 3-[5-(4-methanesulfonyl-piperazin-1-ylmethyl)-1H-indol-2-yl]-1H-quinolin-2-one (1-11C).

HCl Salt:

Two crystalline salts of 1-11 have been identified: 1-11C and 1-11D. The XRPD of the HCl salt 1-11C (FIG. 3) verify that it is crystalline. DSC showed a melting endotherm at 284° C. The compound contains 5.4% moisture up to 150° C. as evidenced by TGA. This salt also seems to decompose on melting as seen by a sharp drop in weight at melting.

HCl salt 1-11D is also crystalline as witnessed by the X-ray powder diffraction pattern of the material, having multiple diffraction peaks between 5° and 30° 2-theta. DSC shows a melting endotherm of 284.08° C. (rate of 10° C./min). The compound is birefringent under plane polarized light. It is needle-shaped particles of approximately 5–25 micron. The solubility of salt 1-11D was measured in water and various organic solvents. Table VI below summarizes the solubility of the 1-11D suspended in various solvents for 7 days at room temperature.

TABLE VI

Solubility of HCl Salt 1-11D RT for 7 days

| Solvents | Solubility (mg/mL) |
|---|---|
| Water | 0.62 |
| Ethanol | 0.13 |
| Isopropanol | 0.057 |
| Aqueous ETOH | 4.34 |
| Aqueous IPA | 3.99 |

The X-ray powder diffraction data for 1-11D is summarized below:

| | 2-Theta° | Angstrom | Count | % |
|---|---|---|---|---|
| d = 13.07327 | 6.756 | 13.07327 | 1197 | 62.1 |
| d = 10.92179 | 8.089 | 10.92179 | 721 | 37.4 |
| d = 8.87959 | 9.953 | 8.87959 | 971 | 50.4 |
| d = 7.32324 | 12.075 | 7.32324 | 1376 | 71.4 |
| d = 6.88388 | 12.849 | 6.88388 | 1069 | 55.5 |
| d = 6.44424 | 13.730 | 6.44424 | 1010 | 52.4 |
| d = 6.16135 | 14.364 | 6.16135 | 853 | 44.3 |
| d = 5.95917 | 14.854 | 5.95917 | 1056 | 54.8 |

-continued

| | 2-Theta° | Angstrom | Count | % |
|---|---|---|---|---|
| d = 5.81946 | 15.212 | 5.81946 | 1481 | 76.9 |
| d = 5.51333 | 16.062 | 5.51333 | 1556 | 80.7 |
| d = 5.42028 | 16.340 | 5.42028 | 1009 | 52.4 |
| d = 5.27926 | 16.780 | 5.27926 | 1129 | 58.6 |
| d = 5.13623 | 17.250 | 5.13623 | 721 | 37.4 |
| d = 4.84647 | 18.290 | 4.84647 | 1927 | 100.0 |
| d = 4.69650 | 18.880 | 4.69650 | 987 | 51.2 |
| d = 4.63537 | 19.131 | 4.63537 | 1010 | 52.4 |
| d = 4.49882 | 19.717 | 4.49882 | 1239 | 64.3 |
| d = 4.36248 | 20.340 | 4.36248 | 681 | 35.3 |
| d = 4.27994 | 20.737 | 4.27994 | 1764 | 91.5 |
| d = 4.12084 | 21.547 | 4.12084 | 729 | 37.8 |
| d = 3.97380 | 22.354 | 3.97380 | 811 | 42.1 |
| d = 3.86205 | 23.009 | 3.86205 | 553 | 28.7 |
| d = 3.70294 | 24.013 | 3.70294 | 1012 | 52.5 |
| d = 3.66870 | 24.240 | 3.66870 | 842 | 43.7 |
| d = 3.53317 | 25.185 | 3.53317 | 1380 | 71.6 |
| d = 3.48450 | 25.542 | 3.48450 | 1161 | 60.2 |
| d = 3.31645 | 26.860 | 3.31645 | 962 | 49.9 |
| d = 3.21463 | 27.728 | 3.21463 | 485 | 25.2 |
| d = 3.10080 | 28.767 | 3.10080 | 826 | 42.9 |
| d = 3.03001 | 29.454 | 3.03001 | 390 | 20.2 |
| d = 2.98281 | 29.931 | 2.98281 | 556 | 28.9 |
| d = 2.95392 | 30.231 | 2.95392 | 675 | 35.0 |
| d = 2.90366 | 30.767 | 2.90366 | 602 | 31.2 |
| d = 2.84488 | 31.419 | 2.84488 | 403 | 20.9 |
| d = 2.75928 | 32.420 | 2.75928 | 477 | 24.8 |
| d = 2.70643 | 33.071 | 2.70643 | 472 | 24.5 |
| d = 2.43879 | 36.824 | 2.43879 | 345 | 17.9 |

Example 2

Salts of 3-[5-(4-Methyl-5-oxo-[1,4]diazepan-1-ylmethyl)-1H-indol-2-yl]-1H-quinolin-2-one 2-1

2-1 was prepared by simple modifications of the protocols described below to make 3-10.

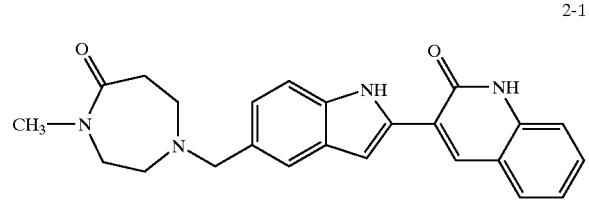

2-1

$^1$H NMR (400 MHz, DMSO-d$_6$) δ 12.16 (s, 1H), 11.53 (s, 1H), 8.52 (s, 1H), 7.73 (d, 1H, J=7.5 Hz), 7.52 (dt, 1H, J=8.5, 1.0 Hz), 7.46 (d, 1H, J=9.0 Hz), 7.45 (s, 1H), 7.38 (d, 1H, J=8.0 Hz), 7.29 (s, 1H), 7.25 (t, 1H, J=7.5 Hz), 7.08 (dd, 1H, J=8.0, 1.0 Hz), 3.61 (s, 2H), 3.42 (m, 2H), 2.83 (s, 3H), 2.54–2.50 (m, 6H);

Mesylate salt 2-1A was prepared by simple modifications of the protocols described below to make 3-10B.

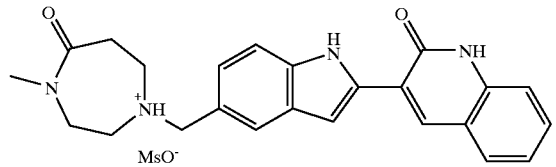

2-1A

4-Methyl-5-oxo-1-[2-(2-oxo-1,2-dihydro-quinolin-3-yl)-1H-indol-5-ylmethyl]-[1,4]diazepan-1-ium; methanesulfonate; methanesulfonate (2-1A)

$^1$H NMR (300 MHz, DMSO-d$_6$) δ 12.21 (s, 1H), 11.82 (s, 1H), 10.81 (br s, 1H), 8.61 (s, 1H), 7.76 (s, 1H), 7.74 (d, 1H, J=8.5 Hz), 7.60 (d, 1H, J=8.0 Hz), 7.54 (t, 1H, J=8.0), 7.40 (d, 1H, J=8.0 Hz), 7.39 (s, 1H), 7.31 (dd, 1H, J=8.5, 1.5 Hz), 7.26 (t, 1H, J=7.5 Hz), 4.41 (m, 2H), 4.04 (m, 1H), 3.47 (m, 3H), 3.24–3.08 (m, 3H), 2.87 (s, 3H), 2.55 (m, 1H).

HCl salt 2-1B was prepared by simple modifications of the protocols described below to make 3-10A.

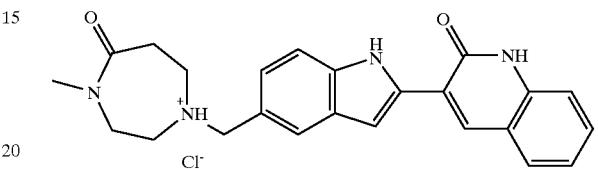

2-1B

4-Methyl-5-oxo-1-[2-(2-oxo-1,2-dihydro-quinolin-3-yl)-1H-indol-5-ylmethyl]-[1,4]diazepan-1-ium; methanesulfonate; chloride (2-1B)

$^1$H NMR (500 MHz, DMSO-d$_6$) δ 12.21 (s, 1H), 11.82 (s, 1H), 10.81 (br s, 1H), 8.61 (s, 1H), 7.76 (s, 1H), 7.74 (d, 1H, J=8.5 Hz), 7.60 (d, 1H, J=8.0 Hz), 7.54 (t, 1H, J=8.0), 7.40 (d, 1H, J=8.0 Hz), 7.39 (s, 1H), 7.31 (dd, 1H, J=8.5, 1.5 Hz), 7.26 (t, 1H, J=7.5 Hz), 4.41 (m, 2H), 4.04 (m, 1H), 3.47 (m, 3H), 3.24–3.08 (m, 3H), 2.87 (s, 3H), 2.55 (m, 1H).

Characteristics of the Free Base

The free base 2-1 is a yellow powder. Examination under polarized light by optical microscopy revealed that the crystals are birefringent indicating crystallinity. The crystals appear plate-like with most of the particles below 10 microns. TGA analysis with a scan rate of 10° C./min to 350° C. shows the solid loses 0.51% weight up to 125° C. and loses weight more rapidly past 275° C. DSC analysis with a scan rate of 10° C./min to 350° C. shows a reversible endotherm at 292° C. The aqueous solubility was measured using HPLC to quantitate the compound in suspension. The solubility at room temperature is 0.028 mg/mL.

Mesylate Salt

The mesylate salt 2-1A is a yellow powder. Examination under polarized light by optical microscopy shows that the solid is not birefringent, indicating that it is amorphous. TGA analysis at a scan rate of 10° C./min to 350° C. shows the solid loses 2.74% weight up to 125° C. and decomposes above 250° C. DSC analysis with a scan rate of 10° C./min to 350° C. does not show any reversible endotherm confirming that the solid is amorphous. A broad non-reversible endotherm centered around 87° C. is attributed to loss of solvent/moisture. The aqueous solubility was measured using HPLC to quantitate the compound. The aqueous solubility at room temperature is greater than 9.89 mg/mL. In the time scale of the experiment (24 hours) no crystallization was observed.

HCl Salt

The HCl salt 2-1B was also a yellow powder. Examination under polarized light by optical microscopy showed that the solid contained some particles that were birefringent and particles that are not birefringent. This indicates the presence of both amorphous and crystalline material. TGA with a scan rate of 10° C./min to 350° C. shows the solid loses 2.4% weight up to 125° C. and decomposes above 250° C. DSC analysis at a scan rate of 10° C./min to 350° C. shows a reversible endotherm at 231° C. indicating the existence of some crystalline material. The aqueous solubility was measured using HPLC to quantitate the compound. The aqueous solubility at room temperature is greater than 10.21 mg/mL. In the time scale of the experiment (24 hours) the solid did not crystallize out of this highly concentrated solution.

Example 3

Salts of 3-{5-[4-(2-Hydroxy-ethanoyl)-piperazin-1-ylmethyl]-1H-indol-2-yl}-1H-quinolin-2-one

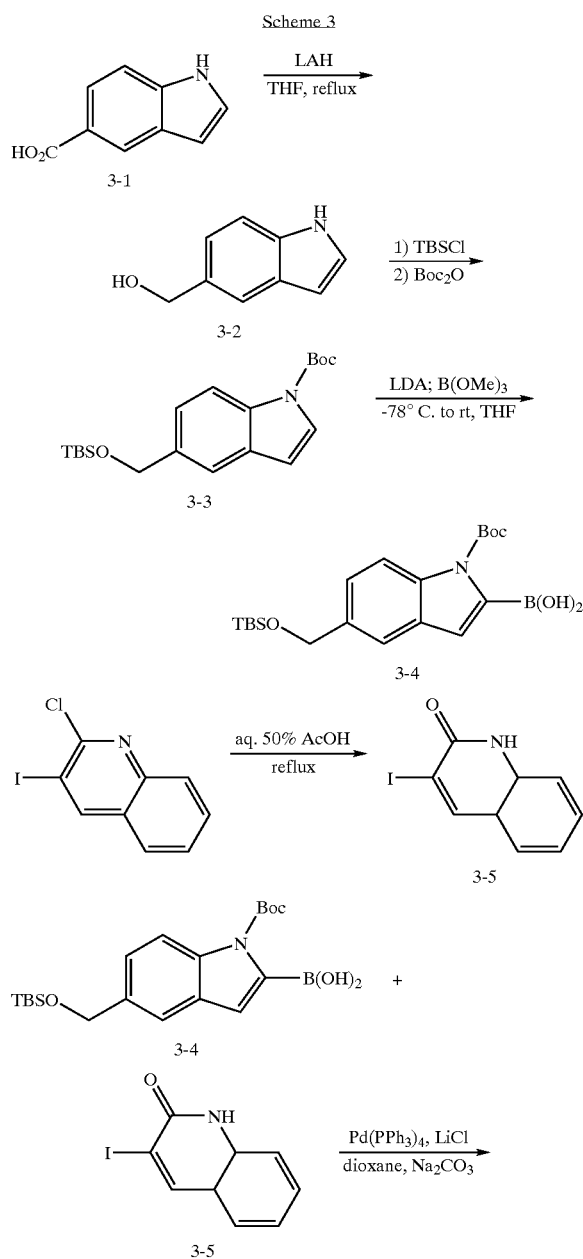

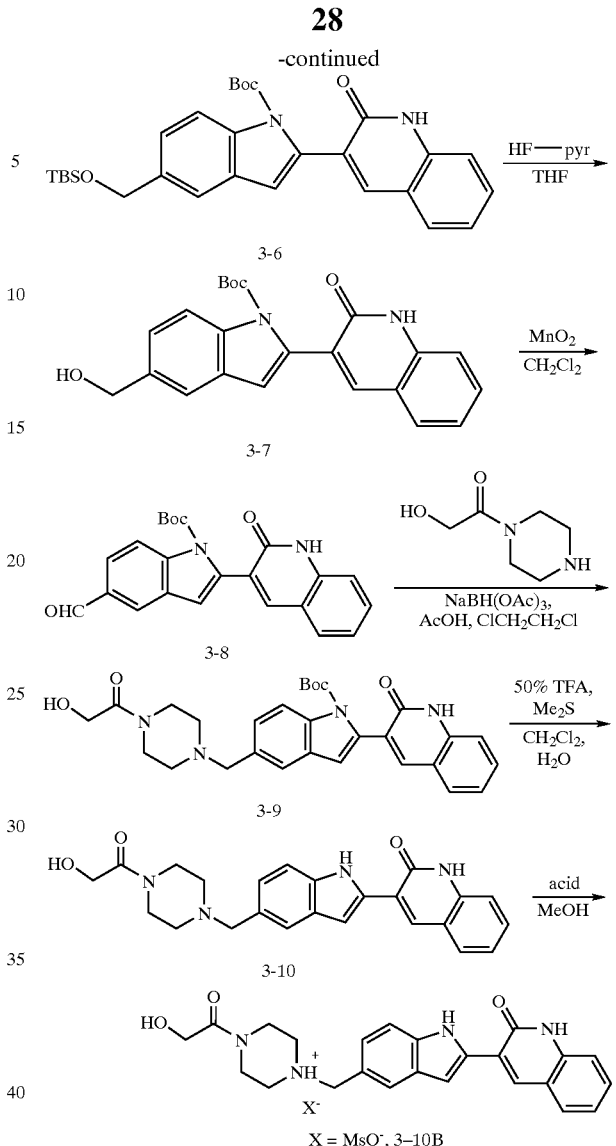

(1H-Indol-5-yl)-methanol (3-2)

To a mechanically stirred solution of 1H-Indole-5-carboxylic acid (3-1, 20.01 g, 124 mmol) in tetrahydrofuran (500 mL) was added at ambient temperature slowly a solution of 1M-LAH in toluene (186 mL, 186 mmol, 1.5 equiv). The reaction mixture was heated at reflux for 1 h, quenched with ice, partitioned between EA and saturated aqueous NaHCO$_3$. The organic layer was washed with brine, separated, dried (MgSO$_4$) ans concentrated in vacuo. The crude product solidified upon standing under the reduced pressure. The crude solid was suspended in hexanes (200 mL) and ethyl acetate (10 mL), stirred overnight, collected by filtration and air-dried to afford the desired product as a light brown solid. $^1$H NMR (400 MHz, CDCl$_3$) δ 8.24 (br s, 1H), 7.62 (s, 1H), 7.36 (d, 1H, J=8.4 Hz), 7.23 (d, 1H, J=8.4 Hz), 7.20 (s, 1H), 6.54 (s, 1H), 4.75 (s, 2H), 1.68 (s, 1H).

5-(tert-Butyl-dimethyl-silanyloxymethyl)-indole-1-carboxylic acid tert-butyl ester (3-3)

A stirred solution of (1H-Indol-5-yl)-methanol (3-2, 16.5 g, 112.1 mmol) in dichloromethane (300 mL) was subsequently treated at ambient temperature with diisopropylethylamine (39 mL, 224.2 mmol, 2 equiv), tert-butyldimethylsilyl chloride (18.6 g, 123.3 mmol, 1.1 equiv), and 4-(N,N-dimethylamino)pyridine (1.37 g, 11.2 mmol, 0.1 equiv). The reaction mixture was stirred at rt for 30 min, concentrated in vacuo, partitioned between ethyl acetate and 0.5N-HCl. The organic layer was washed with brine, separated, dried (MgSO$_4$), concentrated in vacuo to give the crude silylether as a light brown solid. The crude product and di-tert-butyl dicarbonate (26.9, 123.3 mmol) were dissolved in dichrolomethane (300 mL) and stirred at ambient temperature in the presence of 4-(N,N-dimethylamino)pyridine (1.37 g, 11.2 mmol) for 2 h. The reaction mixture was concentrated in vacuo, partitioned between ethyl acetate and 0.5N-HCl. The organic layer was washed with brine, separated, dried (MgSO$_4$) and concentrated in vacuo to give the crude oil. Chromatography (SiO$_2$, 10% ethyl acetate in hexanes) afforded 5-(tert-Butyl-dimethyl-silanyloxymethyl)-indole-1-carboxylic acid tert-butyl ester (3-3, 38.6 g, 95%) as a white solid; $^1$H NMR (400 MHz, CDCl$_3$) δ 7.97 (d, 1H, J=8.0 Hz), 7.47 (d, 1H, J=3.2 Hz), 7.41 (s, 1H), 7.15 (d, 1H, J=7.7 Hz), 6.44 (d, 1H, J=3.6 Hz), 4.72 (s, 2H), 1.56 (s, 9H), 0.84 (s, 9H), 0.00 (s, 6H).

5-(tert-Butyl-dimethyl-silanyloxymethyl)-indole-1-tert-butyloxycarbonylindole-2-boronic acid (3-4)

To a stirred solution of 5-(tert-Butyl-dimethyl-silanyloxymethyl)-indole-1-carboxylic acid tert-butyl ester (3-3, 38.6 g, 106.7 mmol) in tetrahydrofuran (400 mL) was slowly added at −78 deg C. a solution of lithiun diisopropylamide in tetrahydrofuran (2M, 80.1 mL, 160.1 mmol, 1.5 equiv). The reaction mixture was stirred at the same temperature for 1 h, treated with trimethylborate, warmed up to ambient temperature, and partitioned between ethyl acetate and 0.5N-HCl. The organic layer was washed with brine, separated, dried (MgSO$_4$) and concentrated in vacuo to give the crude solid. Trituration of the crude product with hexanes followed by filtration and air-drying afforded the desired boronic acid (3-4, 41.3 g, 95%) as a white powder; $^1$H NMR (400 MHz, CDCl$_3$) δ 7.96 (d, 1H, J=6.8 Hz), 7.54 (s, 1H), 7.47 (s, 1H), 7.32 (d, 1H, J=6.8 Hz), 7.10 (s, 1H), 4.82 (s, 2H), 1.74 (s, 9H), 0.95 (s, 9H), 0.11 (s, 6H).

3-Iodo-1H-quinolin-2-one (3-5)

The 2-chloro-3-iodoquinoline (30.0 g) was weighed into a 250 mL flask and suspended in of 50% aqueous acetic acid (125 mL). The mixture was heated to 100 C and allowed to reflux for 16 h to completion by TLC analysis of the crude reaction mixture. The mixture was allowed to cool to ambient temperature followed by dilution with 200 mL of water. The resulting a suspension of the desired product was isolated by vacuum filtration follows by washing with water (50 mL). The water and traces of acetic acid were removed under vacuum for 5 h to afford the desired quinolinone as a tan powder (5-5, 26.5 g, 94%); $^1$H NMR (500 MHz, CDCl$_3$) δ 12.13 (br s, 1H), 8.71 (s, 1H), 7.65 (d, 1H, J=7.5 Hz), 7.54 (m, 1H), 7.31 (d, 1H, J=8.0 Hz), 7.20 (m, 1H).

5-Hydroxymethyl-2-(2-oxo-1,2-dihydro-quinolin-3-yl)-indole-1-carboxylic acid tert-butyl ester (5-7)

A stirred mixture of the iodoquinolinone (5-5, 10 g, 36.9 mmol, 1 equiv), the boronic acid (5-4, 7.5 g, 18.45 mmol, 0.5 equiv), tetrakis(triphenylphosphine)palladium (1.71 g, 1.48 mmol, 0.04 equiv), and lithium chloride (4.69 g, 110.7 mmol, 3 equiv) in dioxane/2M-aqueous Na$_2$CO$_3$ was degassed and heated at 80 deg C. until the boronic acid is not detected by thin layer chromatography. Additional boronic acid (0.2 equiv at a time) was added to the reaction mixture until all the iodoquinolinone (5-5) was consumed completely (1.5 equivalent of the boronic acid, 5-4, in total, was required). The reaction mixture was partitioned between ethyl acetate and saturated aqueous NaHCO$_3$. The organic layer was washed with brine, separated, dried (MgSO$_4$) and concentrated in vacuo. The crude oil (5-6) was dissolved in tetrahydrofuran (100 mL), transferred to the PEG bottle, treated at 0 deg C. with HF-pyridine (15 mL) and stirred for 1 h at ambient temperature. The reaction mixture was partitioned between ethyl acetate and saturated aqueous NaHCO$_3$. The organic layer was washed with brine, separated, dried (MgSO$_4$) and concentrated in vacuo. The crude solid was triturated with ethyl acetate and hexanes, collected by filtration and air-dried to afford the desired product (5-7) as a light yellow solid (12.4 g, 86%); $^1$H NMR (500 MHz, DMSO-d$_6$) δ 12.1 (s, 1H), 8.07 (s, 1H), 8.03 (d, 1H, J=8.5 Hz), 7.74 (d, 1H, J=7.5 Hz), 7.55 (s, 1H), 7.52 (t, 1H, J=7.5 Hz), 7.35 (d, 1H, J=8.5 Hz), 7.30 (d, 1H, J=7.5 Hz), 7.22 (t, 1H, J=7.5 Hz), 6.77 (s, 1H), 5.21 (t, 1H, J=5.5 Hz), 4.60 (d, 2H, J=5.5 Hz), 1.35 (s, 9H).

5-Formyl-2-(2-oxo-1,2-dihydro-quinolin-3-yl)-indole-1-carboxylic acid tert-butyl ester (5-8)

The pre-activated MnO$_2$ (34.5 g, 15 equiv) and the alcohol (5-7, 10.32 g, 1.0 equiv) were weighed into a 1 liter flask and suspended in dry dichloromethane (500 mL). The reaction mixture was heated to 45 deg C. and was complete by thin layer chromatography after 1 h. The mixture was allowed to cool to ambient temperature and the manganese oxide(s) were removed by vacuum filtration. The resulting pad of oxides on the filter were triturated with hot THF and the solvent filtered through under vacuum to remove any product from the oxides. The resulting filtrate was concentrated in vacuo to afford the crude aldehyde as a yellow solid. The solid was triturated with methanol (10 mL) and ethyl acetate (15 mL) followed by vacuum filtration to isolate the pure product. The light-yellow aldehyde was dried under vacuum (5-8, 9.84 g, 96%); $^1$H NMR (500 MHz, DMSO-d$_6$) δ 12.15 (s, 1H), 10.08 (s, 1H), 8.26 (d, 1H, J=1.5 Hz), 8.24 (d, 1H, J=8.5 Hz), 8.15 (s, 1H), 7.90 (dd, 1H, J=8.5, 1.5 Hz), 7.77 (d, 1H, J=7.5 Hz), 7.55 (m, 1H), 7.37 (d, 1H, J=8.5 Hz), 7.24 (m, 1H), 7.01 (s, 1H).

5-[4-(2-Hydroxy-ethanoyl)-piperazin-1-ylmethyl]-2-(2-oxo-1,2-dihydro-quinolin-3-yl)-indole-1-carboxylic acid tert-butyl ester (5-9)

To a stirred solution of the aldehyde (5-8, 2.01 g, 5.15 mmol, 1 equiv) and N-(2-hydroxyacetyl)piperazine (2.97 g, 20.60 mmol, 4 equiv) in dichloroethane (400 mL) was added at ambient temperature acetic acid (1.2 mL). The reaction mixture was treated with sodium triacetoxyborohydride and stirred for 3 h. The reaction stopped at 76% of conversion and treated with MgSO$_4$ and additional 1 g of the hydride. After further stirring for 1 h the reaction was complete. The reaction mixture was partitioned between ethyl acetate and saturated aqueous NaHCO$_3$. The organic layer was once again washed with saturated aqueous NaHCO$_3$, and then with brine, separated, dried with (Na$_2$SO$_4$) and concentrated in vacuo. The crude solid was dissolved in N,N-dimethylformamide and treated with the activated carbon. The filtrate solution (celite) was concentrated to syrup which was quickly triturated with methanol (100 mL). The resulting solid was collected by filtration, redissolved in N,N-dimethylformamide, concentrated to syrup, triturated with methanol (100 mL), collected by filtration and vacuum-dried to give 5-[4-(2-hydroxy-ethanoyl)-piperazin-1-ylmethyl]-2-(2-oxo-1,2-dihydro-quinolin-3-yl)-indole-1-carboxylic acid tert-butyl ester (5-9, 1.51 g, 57%) as a white powder; $^1$H NMR (500 MHz, DMSO-$d_6$) δ 12.24 (br s, 1H), 8.21 (d, 1H, J=8.7 Hz), 7.91 (s, 1H), 7.61 (d, 1H, J=6.9 Hz), 7.52 (s, 1H), 7.49 (m, 1H), 7.36 (d, 1H, J=8.1 Hz), 7.33 (dd, 1H, J=8.4, 1.5 Hz), 7.24 (m, 1H), 6.67 (s, 1H), 4.15 (s, 2H), 3.69 (m, 2H), 3.65 (s, 2H), 3.28 (m, 2H), 2.49 (m, 4H), 1.40 (s, 9H).

3-{5-[4-(2-Hydroxy-ethanoyl)-piperazin-1-ylmethyl]-1H-indol-2-yl}-1H-quinolin-2-one (5-10)

A mixture of 5-(4-Methanesulfonyl-piperazin-1-ylmethyl)-2-(2-oxo-1,2-dihydro-quinolin-3-yl)-indole-1-carboxylic acid tert-butyl ester (5-9, 1.05 g, 2.033 mmol), dimethylsulfide (1.2 mL), water (0.6 mL) and trifluoroacetic acid (40 mL) in dichloromethane (40 mL) was stirred for 1.5 h. The reaction mixture was concentrated in vacuo, partitioned between ethyl acetate and saturated aqueous NaHCO$_3$. The organic layer was washed with brine, separated, dried (Na$_2$SO$_4$), and concentrated in vacuo. The resulting crude solid was purified by reverse-phase liquid chromatography (H$_2$O/CH$_3$CN gradient with 0.1% TFA present) to give trifluoroacetic acid salt of 5-10. All the fractions containing the desired product was partitioned between ethyl acetate and saturated aqueous NaHCO$_3$. The organic layer was washed with brine, separated, dried (Na$_2$SO$_4$), and concentrated in vacuo to give 3-{5-[4-(2-hydroxy-ethanoyl)-piperazin-1-ylmethyl]-1H-indol-2-yl}-1H-quinolin-2-one (5-10, 737 mg, 87%) as a bright yellow solid; $^1$H NMR (500 MHz, DMSO-$d_6$) δ 12.16 (br s, 1H), 11.53 (s, 1H), 8.52 (s, 1H), 7.73 (d, 1H, J=7.5 Hz), 7.52 (dt, 1H, J=8.5, 1.0 Hz), 7.47 (d, 1H, J=9.0 Hz), 7.46 (s, 1H), 7.38 (d, 1H, J=8.0 Hz), 7.29 (d, 1H, J=1.0 Hz), 7.25 (t, 1H, J=7.5 Hz), 7.08 (dd, 1H, J=8.0, 1.0 Hz), 4.51 (t, 1H, J=5.5 Hz), 4.06 (d, 1H, J=5.5 Hz) 3.55 (s, 2H), 3.46 (m, 2H), 3.32 (m, 2H), 2.36 (m, 4H).

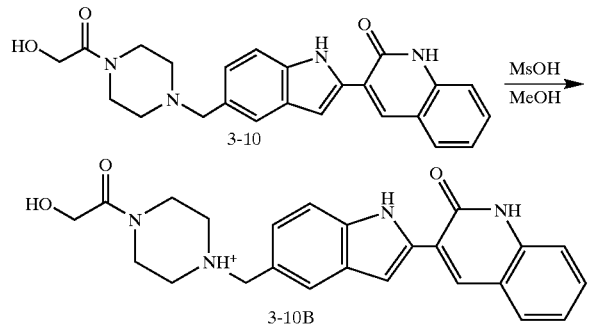

4-(2-Hydroxy-ethanoyl)-1-[2-(2-oxo-1,2-dihydro-quinolin-3-yl)-1H-indol-5-ylmethyl]-piperazin-1-ium; methanesulfonate (3-10B)

To a stirred suspension of the free base (3-10, 9.22 mmol) in MeOH (2 L) was slowly added at rt a 0.3M-MsOH (30.73 mL, 1.0 equiv., 9.22 mmol). After all the solid dissolved, the mixture was filtered into a rb flask and concentrated on vacuo (with the bath temp ~10° C.). The resulting solid was suspended with 200 mL of ethyl acetate, filtered, dried to afford the desired Ms salt (3-10B); $^1$H NMR (500 MHz, DMSO-$d_6$) δ 12.21 (s, 1H), 11.81 (s, 1H), 9.70 (br s, 1H), 8.59 (s, 1H), 7.75 (d, 1H, J=8.0 Hz), 7.72 (s, 1H), 7.62 (d, 1H, J=8.5 Hz), 7.54 (t, 1H, J=7.5), 7.39 (d, 1H, J=8.0 Hz), 7.39 (s, 1H), 7.27 (t, 1H, J=7.5 Hz), 7.22 (d, 1H, J=8.5 Hz), 4.83 (br s, 1H), 4.42 (br s, 3H), 4.17 (d, 1H, J=15.0 Hz), 4.07 (d, 1H, J=15.0 Hz), 3.94 (d, 1H, J=13.5 Hz), 3.34 (s, 3H), 3.10 (m, 1H), 2.97 (m, 2H), 2.30 (m, 3H).

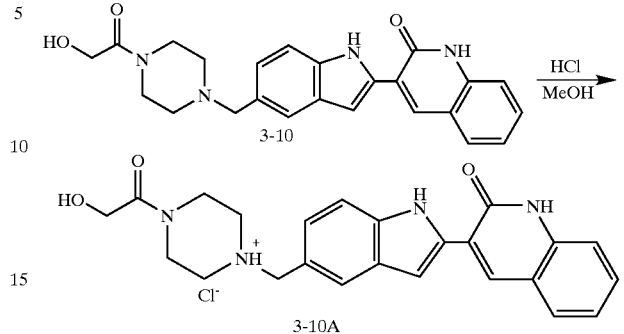

4-(2-Hydroxy-ethanoyl)-1-[2-(2-oxo-1,2-dihydro-quinolin-3-yl)-1H-indol-5-ylmethyl]-piperazin-1-ium; chloride (3-10A)

To a stirred suspension of the free base (3-10, 0.465 mmol) in MeOH (200 mL) was slowly added at rt a 1N-HCl (0.47 mL, 1.0 equiv., 0.465 mmol). After all the solid dissolved, the mixture was filtered into a rb flask and concentrated on vacuo (with the bath temp ~10° C.). The resulting solid was suspended with 200 mL of ethyl acetate, filtered, dried to afford the desired HCl salt (3-10A); $^1$H NMR (500 MHz, DMSO-$d_6$) δ 12.21 (s, 1H), 11.82 (s, 1H), 10.59 (br s, 1H), 8.60 (s, 1H), 7.75 (s, 1H), 7.74 (d, 1H, J=8.5 Hz), 7.61 (d, 1H, J=8.5 Hz), 7.54 (t, 1H, J=8.5), 7.40 (d, 1H, J=8.5 Hz), 7.39 (s, 1H), 7.29 (m, 1H), 7.26 (t, 1H, J=7.0 Hz), 4.40 (m, 3H), 4.16 (d, 1H, J=14.5 Hz), 4.06 (d, 1H, J=14.5 Hz), 3.92 (d, 1H, J=13.0 Hz), 3.42 (m, 2H), 3.17 (s, 1H), 3.06 (m, 2H), 2.96 (m, 1H).

Characteristics of the Free Base

The free base is a yellow powder which contains particles that are birefringent under polarized light indicating the presence of crystalline material. TGA analysis with a scan rate of 10° C./min to 350° C. shows the solid loses 0.67% weight up to 125° C. and decomposes above 300° C. DSC analysis with a scan rate of 10° C./min to 350° C. shows a reversible endotherm at 299° C. indicating that the solid decomposes upon melting. The aqueous solubility was measured using HPLC to quantitate the compound in an aqueous suspension. The aqueous solubility at room temperature is 0.0635 mg/mL.

HCl Salt

The HCl salt is also a yellow solid, which contains particles that are birefringent under polarized light indicating the presence of crystalline material. TGA analysis with a scan rate of 10° C./min to 350° C. shows the solid loses 4.92% weight up to 125° C. and decomposes above 300° C. DSC analysis with a scan rate of 10° C./min to 350° C. shows a reversible endotherm at 235° C. The aqueous solubility was measured using HPLC to quantitate the compound in suspension. The aqueous solubility at room temperature is 1.31 mg/mL.

Mesylate Salt

The yellow, mesylate salt was examined under polarized light by optical microscopy. The solid does not show birefringent particles under polarized light indicating the presence of amorphous material. TGA analysis with a scan rate of 10° C./min to 350° C. shows the solid loses 4.89% weight up to 125° C. and decomposes above 300° C. DSC analysis with a scan rate of 10° C./min to 350° C. shows a reversible endotherm at 153° C. It is possible that the small amount of crystalline solid went undetected by optical microscopy. The aqueous solubility was measured using HPLC to quantitate the compound in suspension. The aqueous solubility at room temperature is 2.43 mg/mL.

Example 4

Salts of 3-(5-{2-[(2-methoxyethyl)(methyl)amino] ethoxy}-1H-indol-2-yl)-2(1H)-quinolinone 4-9

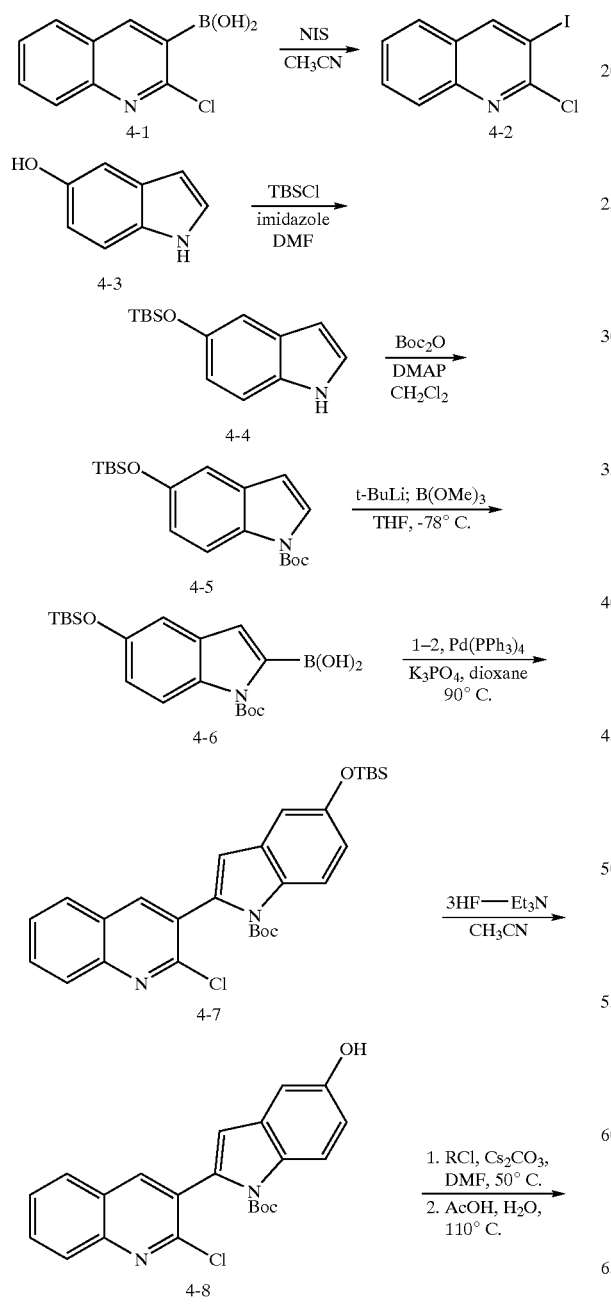

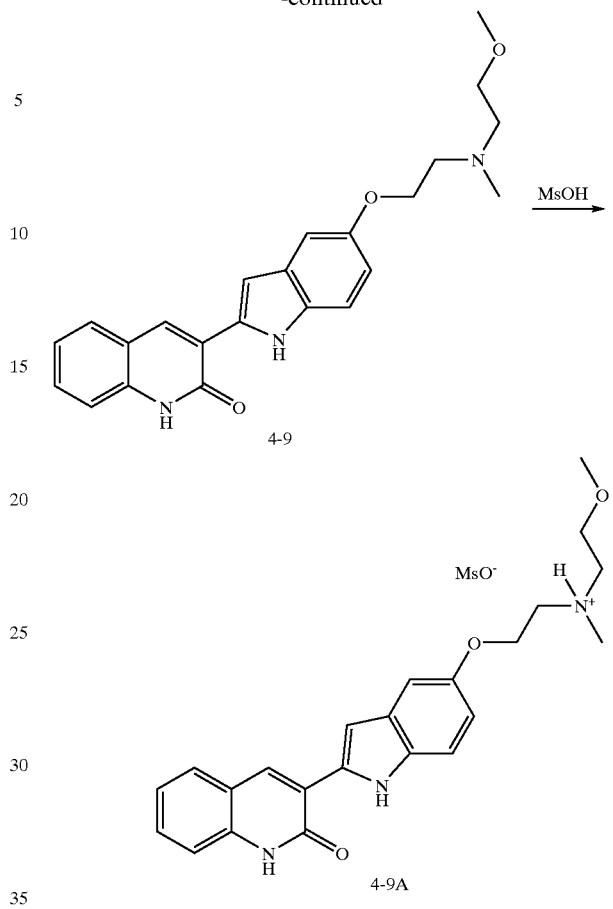

2-chloro-3-iodo-quinoline (1-2)

A suspension of 3-(2-chloro)-quinolineboronic acid (1-1, 5.05 g, 24.3 mmol, 1 equiv, prepared by the method of Marsais, F; Godard, A.; Queguiner, G. *J. Heterocyclic Chem.* 1989, 26, 1589–1594) and N-iodosuccinimide (5.48 g, 24.4 mmol, 1.00 equiv) in acetonitrile (300 mL) was stirred at 23° C. in the dark for 20 hours. The reaction mixture was concentrated to dryness, and the resulting yellow solid was partitioned between saturated aqueous sodium bicarbonate solution and dichloro-methane. The organic layer was washed with water, then dried over magnesium sulfate and concentrated to give 2-chloro-3-iodo-quinoline as a pale yellow solid. $^1$H NMR (400 MHz, CDCl$_3$) δ 8.67 (s, 1H), 7.99 (br d, 1H, J=8.4 Hz), 7.75 (br t, 1H, J=7.7 Hz), 7.72 (br d, 1H, J=7.8 Hz), 7.57 (br t, 1H, J=7.6 Hz).

5-(tert-butyl-dimethyl-silanyloxy)-1H-indole (1-4)

A solution of 5-hydroxyindole (1-3, 5.50 g, 41.3 mmol, 1 equiv), tert-butyldimethylsilyl chloride (7.47 g, 49.6 mmol, 1.20 equiv), and imidazole (7.03 g, 103 mmol, 2.50 equiv) in N,N-dimethylformamide (20 mL) was stirred at 23° C. for 20 hours. The reaction mixture was concentrated, and the residue was partitioned between ethyl acetate and water. The organic layer was washed with water (3×), then dried over magnesium sulfate and concentrated. The residue was purified by flash column chromatography (40% dichloromethane in hexanes, then 60% dichloro-methane in hexanes) to give 5-(tert-butyl-dimethyl-silanyloxy)-1H-indole as a colorless oil which solidified upon standing. $^1$H NMR (400 MHz, CDCl$_3$) δ 8.00 (br s, 1H), 7.22 (d, 1H, J=8.7 Hz), 7.17 (t, 1H, J=2.8 Hz), 7.06 (d, 1H, J=2.3 Hz), 6.76 (dd, 1H, J=8.6, 2.3 Hz), 6.44 (m, 1H), 1.00 (s, 9H), 0.19 (s, 6H).

5-(tert-butyl-dimethyl-silanyloxy)-indole-1-carboxylic acid tert-butyl ester (1-5)

A solution of 5-(tert-butyl-dimethyl-silanyloxy)-1H-indole (1-4, 10.2 g, 41.3 mmol, 1 equiv), di-tert-butyl dicarbonate (14.4 g, 66.0 equiv, 1.60 equiv), and 4-dimethylaminopyridine (1.01 g, 8.25 mmol, 0.200 equiv) in dichloromethane (100 mL) was stirred at 23° C. for 20 hours. The reaction mixture was concentrated, and the residue was purified by flash column chromatography (40% dichloromethane in hexanes) to afford 5-(tert-butyl-dimethyl-silanyloxy)-indole-1-carboxylic acid tert-butyl ester (1-5) as a colorless oil. $^1$H NMR (400 MHz, CDCl$_3$) δ 7.96 (br d, 1H, J=7.5 Hz), 7.54 (br d, 1H, J=3.1 Hz), 6.98 (d, 1H, J=2.4 Hz), 6.83 (dd, 1H, J=9.0, 2.4 Hz), 6.45 (d, 1H, J=3.7 Hz), 1.66 (s, 9H), 1.00 (s, 9H), 0.20 (s, 6H).

1-(tert-butoxycarbonyl)-5-{[tert-butyl(dimethyl)silyl]oxy}-1H-indol-2-ylboronic acid (1-6)

A solution of tert-butyllithium in pentane (1.7 M, 20.7 mL, 35.2 mmol, 1.20 equiv) was added to a solution of 5-(tert-butyl-dimethyl-silanyloxy)-indole-1-carboxylic acid tert-butyl ester (1-5, 10.2 g, 29.3 mmol, 1 equiv) in tetrahydrofuran (100 mL) at −78° C. The resulting light-brown solution was stirred at −78° C. for 30 minutes, then trimethylborate (6.67 mL, 58.7 mmol, 2.00 equiv) was added. The resulting mixture was warmed to 0° C., then diluted with saturated aqueous ammonium chloride solution (100 mL) and ethyl ether (200 mL). The aqueous layer was made acidic with aqueous 10% potassium hydrogensulfate solution. The organic layer was separated, then washed with brine, dried over magnesium sulfate, and concentrated. The residual yellow solid was triturated with hexanes to give 1-(tert-butoxycarbonyl)-5-{[tert-butyl(dimethyl)silyl]oxy}-1H-indol-2-ylboronic acid (1-6) as an off-white solid. $^1$H NMR (400 MHz, CDCl$_3$) δ 7.84 (d, 1H, J=8.9 Hz), 7.37 (s, 1H), 7.01 (d, 1H, J=2.4 Hz), 6.97 (br s, 2H), 6.88 (dd, 1H, J=9.0, 2.4 Hz), 1.73 (s, 9H), 1.00 (s, 9H), 0.20 (s, 6H).

tert-butyl 5-{[tert-butyl(dimethyl)silyl]oxy}-2-(2-chloro-3-quinolinyl)-1H-indole-1-carboxylate (1-7)

A deoxygenated mixture of 1-(tert-butoxycarbonyl)-5-{[tert-butyl(dimethyl)silyl]oxy}-1H-indol-2-ylboronic acid (1-6, 4.10 g, 10.5 mmol, 1 equiv), 2-chloro-3-iodo-quinoline (1-2, 3.64 g, 12.6 mmol, 1.20 equiv), potassium phosphate (6.67 g, 31.4 mmol, 3.00 equiv), and tetrakis(triphenylphosphine)palladium (0.605 g, 0.524 mmol, 0.050 equiv) in dioxane (100 mL) was heated at 90° C. for 20 hours. The reaction mixture was cooled, then partitioned between a mixture of water and ethyl acetate. The organic layer was separated, washed with brine, dried over magnesium sulfate, and concentrated. The residue was purified by flash column chromatography (20% dichloromethane in hexanes, grading to 90% dichloromethane in hexanes) to give tert-butyl 5-{[tert-butyl(dimethyl)silyl]oxy}-2-(2-chloro-3-quinolinyl)-1H-indole-1-carboxylate (1-7) as a tan-colored foam. $^1$H NMR (400 MHz, CDCl$_3$) δ 8.16 (s, 1H), 8.15 (d, 1H, J=9.0 Hz), 8.07 (d, 1H, J=8.2 Hz), 7.86 (d, 1H, J=7.8 Hz), 7.77 (br t, 1H, J=8.4 Hz), 7.60 (br t, 1H, J=8.1 Hz), 7.03 (d, 1H, J=2.4 Hz), 6.92 (dd, 1H, J=9.0, 2.4 Hz), 6.55 (s, 1H), 1.26 (s, 9H), 1.02 (s, 9H), 0.23 (s, 6H).

tert-butyl 2-(2-chloro-3-quinolinyl)-5-hydroxy-1H-indole-1-carboxylate (1-8)

A solution of tert-butyl 5-{[tert-butyl(dimethyl)silyl]oxy}-2-(2-chloro-3-quinolinyl)-1H-indole-1-carboxylate (1-7, 2.50 g, 4.91 mmol, 1 equiv) and triethylamine trihydrofluoride (3.60 mL, 22.1 mmol, 4.50 equiv) in acetonitrile (100 mL) was stirred at 23° C. for 20 hours. The reaction mixture was concentrated, and the residue was partitioned between saturated aqueous sodium bicarbonate solution and ethyl acetate. The organic layer was washed with brine, dried over magnesium sulfate and concentrated to tert-butyl 2-(2-chloro-3-quinolinyl)-5-hydroxy-1H-indole-1-carboxylate (1-8) as a tan colored foam (2.1 g, 100%). $^1$H NMR (400 MHz, CDCl$_3$) δ 8.18 (d, 1H, J=9.0 Hz), 8.17 (s, 1H), 8.07 (d, 1H, J=8.4 Hz), 7.86 (d, 1H, J=8.1 Hz), 7.77 (br t, 1H, J=8.4 Hz), 7.61 (br t, 1H, J=8.1 Hz), 7.03 (d, 1H, J=2.6 Hz), 6.93 (dd, 1H, J=8.8, 2.6 Hz), 6.55 (s, 1H), 1.26 (s, 9H).

3-(5-{2-[(2-methoxyethyl)(methyl)amino]ethoxy}-1H-indol-2-yl)quinolin-2(1H)-one (1-9)

A mixture of tert-butyl 2-(2-chloro-3-quinolinyl)-5-hydroxy-1H-indole-1-carboxylate (1-8, 1.50 g, 3.80 mmol, 1 equiv), 2-chloro-N-(2-methoxyethyl)-N-methylethanamine (720 mg, 4.75 mmol, 1.25 equiv), and cesium carbonate (3.09 g, 9.50 mmol, 2.50 equiv) in N, N-dimethylformamide (20 mL) was heated at 70° C. for 5 hours. The reaction mixture was concentrated, and the residue was partitioned between water and ethyl acetate. The organic layer was washed with water then brine, dried over magnesium sulfate, and concentrated to give a brown gum. The gum was dissolved in a 1:1 mixture of water and acetic acid (60 mL), and the resulting solution was heated at 100° C. for 18 hours. The reaction mixture was concentrated, and the residue was partitioned between aqueous saturated sodium bicarbonate solution and ethyl acetate. The organic layer was washed with water then brine, dried over magnesium sulfate, and concentrated to give a yellow solid. Purification by flash column chromatography (5% ethanol saturated with ammonia/CH$_2$Cl$_2$, grading to 10% ethanol saturated with ammonia/CH$_2$Cl$_2$) provided 3-(5-{2-[(2-methoxyethyl)(methyl)amino]ethoxy}-1H-indol-2-yl)quinolin-2(1H)-one (1-9) as a yellow solid. $^1$H NMR (400 MHz, CDCl$_3$) δ 11.10 (s, 1H), 9.72 (s, 1H), 8.32 (s, 1H), 7.68 (br d, 1H, J=7.8 Hz), 7.53 (br t, 1H, J=7.6 Hz), 7.35 (d, 1H, J=8.8 Hz), 7.29 (br t, 1H, J=7.8 Hz), 7.24 (br d, 1H, J=8.2 Hz), 7.09 (d, 1H, J=2.2 Hz), 6.97 (d, 1H, J=1.4 Hz), 6.89 (dd, 1H, J=8.6, 2.2 Hz), 4.16 (t, 2H, J=5.9 Hz), 3.54 (t, 2H, J=2.67 (t, 3H, J=5.7 Hz), 3.38 (s, 3H), 2.92 (t, 3H, J=6.0 Hz), 2.73 (t, 3H, J=5.8 Hz), 2.44 (s, 3H).

2-methoxy-N-methyl-N-(2-{[2-(2-oxo-1,2-dihydroquinolin-3-yl)-1H-indol-5-yl]oxy}ethyl)ethanaminium methanesulfonate (4-9A)

Methanesulfonic acid (0.250 mL, 3.83 mmol, 1.00 equiv) was added to a solution of 3-(5-{2-[(2-methoxyethyl)(methyl)amino]ethoxy}-1H-indol-2-yl)quinolin-2(1H)-one (4-9, 1.50 g, 3.83 mmol, 1 equiv) in dichloromethane (100 mL) at 23° C. The mixture was concentrated and the residue was suspended in ethyl ether, filtered, and dried to give 2-methoxy-N-methyl-N-(2-{[2-(2-oxo-1,2-dihydroquinolin-3-yl)-1H-indol-5-yl]oxy}ethyl)ethanaminium methanesulfonate (1-10) as a yellow solid. $^1$H NMR (400 MHz, (CD$_3$)$_2$SO) δ 12.17 (s, 1H), 11.53 (s, 1H), 9.55 (br s, 1H), 8.53 (s, 1H), 7.73 (br d, 1H, J=7.9 Hz), 7.52 (br t, 1H, J=7.6 Hz), 7.47 (d, 1H, J=8.6 Hz), 7.38 (br d, 1H, J=8.2 Hz), 7.25 (br t, 1H, J=7.7 Hz), 7.25 (br s, 1H), 7.15 (d, 1H, J=2.2 Hz), 6.84 (dd, 1H, J=8.6, 2.2 Hz), 4.35 (t, 2H, J=4.9 Hz), 3.71 (t, 3H, J=4.9 Hz), 3.64 (m, 1H), 3.52 (m, 3H), 3.33 (s, 3H), 2.92 (br s, 3H), 2.30 (s, 3H).

This mesylate salt 4-9A, which is a yellow powder, was examined under polarized light by optical microscopy. The crystals appear birefringent under polarized light indicating crystallinity. The crystals appear plate-like with few agglomerates. TGA analysis at a scan rate of 10° C./min to 350° C. shows the solid loses 0.91% weight up to 125° C. and decomposes above 275° C. DSC analysis with a scan rate of 10° C./min to 350° C. shows multiple reversible endotherms (82° C., 151.4° C. and 229° C.). The aqueous solubility was measured using HPLC to quantitate the compound in suspension. The solubility of Salt 4-9A at room temperature is 1.5 mg/mL.

Two forms of the mesylate salt were made: Salt 4-9A above and Salt 4-9B below. Numerous salts of 4-9 were prepared in situ and analyzed using the procedure outlined below, 1) $1.25 \times 10^{-5}$ moles of free base were placed in a centrifuge tube.
2) The free base was then reacted with 1.05 mole equivalents of acid.
3) The reagents were mixed with a Vortex mixer and left to stand at room temperature or warmed if needed to dissolve the solid.
4) 100 μL of water were added to suspend the solid.
5) Tube was then covered with aluminum foil and spun overnight on a rotator.
6) The tube was then spun in a centrifuge for 10 minutes at 10,000 RPM.
7) An aliquot was removed from the sample and dried with nitrogen overnight to produce the solid residue (salt) which was analyzed via microscopy and DCS.
8) The liquid residue from the remaining sample was used to measure pH and determine the concentration of salt by HPLC.

The solubility properties of these salts are summarized in Table VII below.

TABLE VII

Solubility of Salts of 4-9

| Salt | Solubility (mg/mL) | pH |
|---|---|---|
| Free Base | 0.075 | 6.75 |
| Mesylate 4-9B | 22.0 | 5.08 |
| HCl | 22.4 | 2.34 |
| Tartrate | 25.3 | 3.23 |
| Citrate | 19.8 | 3.33 |
| Sulfate | 4.35 | 1.40 |

What is claimed is:

1. A method of treating retinal vascularization which is comprised of administering to a mammal in need of such treatment a therapeutically effective amount of a salt selected from the group consisting of:

A mesylate salt 3-[5-(4-methanesulfonyl-piperazin-1-ylmethyl)-1H-indol-2-yl]-1H-quinolin-2-one; and A chloride salt 3-[5-(4-methanesulfonyl-piperazin-1-ylmethyl)-1H-indol-2-yl]-1H-quinolin-2-one.

2. A method of treating diabetic retinopathy which is comprised of administering to a mammal in need of such treatment a therapeutically effective amount of a salt selected from the group consisting of:

A mesylate salt 3-[5-(4-methanesulfonyl-piperazin-1-ylmethyl)-1H-indol-2-yl]-1H-quinolin-2-one; and A chloride salt 3-[5-(4-methanesulfonyl-piperazin-1-ylmethyl)-1H-indol-2-yl]-1H-quinolin-2-one.

3. A method of treating age-related macular degeneration which is comprised of administering to a mammal in need of such treatment a therapeutically effective amount of a salt selected from the group consisting of:

A mesylate salt 3-[5-(4-methanesulfonyl-piperazin-1-ylmethyl)-1H-indol-2-yl]-1H-quinolin-2-one; and A chloride salt 3-[5-(4-methanesulfonyl-piperazin-1-ylmethyl)-1H-indol-2-yl]-1H-quinolin-2-one.

4. A method of treating an inflammatory disease selected from rheumatoid arthritis, psoriasis, contact dermatitis and delayed hypersensitivity reactions, which is comprised of administering to a mammal in need of such treatment a therapeutically effective amount of a salt selected from the group consisting of:

A mesylate salt 3-[5-(4-methanesulfonyl-piperazin-1-ylmethyl)-1H-indol-2-yl]-1H-quinolin-2-one; and A chloride salt 3-[5-(4-methanesulfonyl-piperazin-1-ylmethyl)-1H-indol-2-yl]-1H-quinolin-2-one.

5. A method of treating bone associated pathologies selected from osteosarcoma, osteoarthritis, and rickets which comprises administering a therapeutically effective amount of which is comprised of administering to a mammal in need of such treatment a therapeutically effective amount of a salt selected from the group consisting of:

A mesylate salt 3-[5-(4-methanesulfonyl-piperazin-1-ylmethyl)-1H-indol-2-yl]-1H-quinolin-2-one; and A chloride salt 3-[5-(4-methanesulfonyl-piperazin-1-ylmethyl)-1H-indol-2-yl]-1H-quinolin-2-one.

* * * * *